(12) United States Patent
During et al.

(10) Patent No.: US 7,723,288 B2
(45) Date of Patent: May 25, 2010

(54) METHODS AND COMPOSITIONS FOR THE TREATMENT OF NEUROLOGICAL DISEASE

(75) Inventors: Matthew J. During, New York, NY (US); Annamaria Vezzani, Milan (IT)

(73) Assignee: Neurologix, Inc., Fort Lee, NJ (US)

( * ) Notice: Subject to any disclaimer, the term of this patent is extended or adjusted under 35 U.S.C. 154(b) by 0 days.

(21) Appl. No.: 10/965,007

(22) Filed: Oct. 14, 2004

(65) Prior Publication Data

US 2005/0136036 A1   Jun. 23, 2005

Related U.S. Application Data

(60) Provisional application No. 60/573,082, filed on May 21, 2004, provisional application No. 60/510,985, filed on Oct. 14, 2003.

(51) Int. Cl.
  *A01N 37/18* (2006.01)
  *A61K 39/00* (2006.01)
(52) U.S. Cl. .................................. 514/2; 424/198.1
(58) Field of Classification Search .................. 514/2; 424/198.1
  See application file for complete search history.

(56) References Cited

U.S. PATENT DOCUMENTS

| | | | | |
|---|---|---|---|---|
| 6,582,692 | B1 * | 6/2003 | Podsakoff et al. | 424/93.2 |
| 6,596,269 | B1 | 7/2003 | Iadarola et al. | |
| 2003/0118552 | A1 * | 6/2003 | Kaspar et al. | 424/93.2 |
| 2003/0228284 | A1 * | 12/2003 | McCown et al. | 424/93.2 |

OTHER PUBLICATIONS

Vezzani et al. (Neuroscience 110(2): 237-243; 2002.*
Thomas et al. Nature Rev./Genet. 4: 346-358; 2003.*
Wilson et al. Adv. Drug Deliv. Rev. 46:205-209; 2001.*
Brockstedt et al. Clinical Immunol. 92:67-75; 1999.*
Bowie, et al. Science, 247: 1306-10, 1990.*
Skolnick et al. TIBTECH 18:34-39, 2000.*
Larhammar Regulatory Peptides 62:1-11; 1996.*
El Meskini et al. Endocrinology 142:864-873; 2001.*
Bryant et al., Use of reconstituted sendai viral envelopes to deliver a NPY-containing adeno-associated virus vector to neuroblastoma and brain cells, J. American Geriatrics Society, vol. 41, No. 10, p. SA2 (1993).
Wu et al., Use of adeno-associated virus vector to express exogenous neuropeptide Y in neural cells, Society for Neuroscience Abstracts, vol. 19, p. 391 (1993).
Kaplitt et al., Adeno-associated virus (AAV) vectors for genetic therapy of neurologic disease, Neurology, vol. 44, Suppl. 2, p. A163, (1994).
de Fiebre et al., Use of reconstituted sendai viral envelopes to deliver a NPY-containing adeno-associated virus vector to neuroblastoma and glial cells in cuture, Society for Neuroscience Abstracts, vol. 18, p. 781, (1992).
Richichi et al., Adeno-Associated Viral Vector (rAAV) Carrying the Neuropeptide Y Gene Induces Long-Lasting Peptide Transduction In Rat Hippocampus And Inhibits Limbic Seizures, Society of Neuroscience Abstracts (Nov. 2002).
Lin et al., Effects of rAAV-mediated NPY and Galanin Overexpression In Rat Hippocampus On Rat Behaviour And Seizure Modulation, Society of Neuroscience Abstracts (Nov. 2001).
Ping et al., Differential Neuropeptide Y gene Expression In Post-Mitotic Versus Dividing Neuroblastoma Cells Driven by an Adeno-Associated Virus Vector, Molecular Brain Research, 24:27-33 (1994) (Abstract Only).
Lin et al., Expression Studies of NPY and Galanin Mediated by RAAV Vectors In Rat Hippocampus, Society of Neuroscience Abstracts (Nov. 2002).
Vezzani et al., Seizure Susceptibility And Epileptogenesis Are Decreased In Transgenic Rats Overexpressing Neuropeptide Y, Neuroscience, 110:237-243 (2002).
Haberman et al., Attenuation Of Seizures and Neuronal Death by Adeno-Associated Virus Vector Galanin Expression and Secretion, Nature Medicine, 9:1076-1080 (2003).
Woldbye et al., Powerful Inhibition Of Kainic Acid Seizures by Neuropeptide Y Via Y5-Like Receptors, Nature Medicine, 3:761-764 (1997).
Vezzani et al., Decreased Seizure Susceptibility In Transgenic Rats Overexpressing Neuropeptide Y, Society of Neuroscience Abstracts (Nov. 2000).
Freese et al., Direct Gene Transfer Into Human Epileptogenic Hippocampal Tissue With An Adeno-Associated Virus Vector: Implications For A Gene Therapy Approach To Epilepsy, Epilepsia, 38:759-766 (1997) (Abstract Only).
Richichi et al., Anticonvulsant And Antiepileptogenic Effects Mediated by Adeno-Associated Virus Vector Neuropeptide Y Expression In The Rat Hippocampus, The Journal of Neuroscience, 24:3051-3059 (2004).
Lin et al., Modulation Of Seizure Activities by rAAV—Mediated Neuropeptide Y Overexpression in the Hippocampus of NPY Receptor Knockout Mice, Society of Neuroscience Abstracts (Nov. 2003).
Foti et al., Adeno-associated virus-mediated expression and constitutive secretion of NPY or NPY 13-36 suppresses seizure activity in vivo, Gene Therapy, 14:1534-1536 (2007).
McCown, Adeno-associated Virus-Mediated Expression and Constitutive Secretion of Galanin Suppresses Limbic Seizure Activity in Vivo, Molecular Therapy, 14:63-68 (2006).
McCown, Adeno-Associated Virus(AAV) Vectors in the CNS, Current Gene Therapy, 5:333-338 (2005).
Lin et al., "Effects Of rAAV-Mediated NPY And Galanin Overexpression In Rat Hippocampus On Rat Behaviour And Seizure Modulation", Society for Neuroscience Abstracts, vol. 27, p. 2014, 2001.

(Continued)

*Primary Examiner*—Fereydoun G Sajjadi
(74) *Attorney, Agent, or Firm*—Nutter McClennen & Fish LLP; George A. Xixis

(57) ABSTRACT

The present invention relates to a method for delivering a nucleic acid sequence encoding neuropeptide Y, or a derivative or functional fragment thereof, to a mammalian nervous system target cell. The expression of exogenous NPY, or a derivative or a functional fragment thereof in the target cell(s) provides therapeutic benefit for subjects afflicted with a neurological disorder.

14 Claims, 8 Drawing Sheets

OTHER PUBLICATIONS

Wu et al., "An AAV Promoter-Driven Neuropeptide Y Gene Delivery System Using Sendai Virosomes For Neurons and Rat Brain", Gene Therapy, vol. 3, pp. 246-253, 1996.

European Search Report, EP Application No. 04 795 081.1, Mailed May 15, 2009.

Wu et al., Differential neuropeptide Y gene expression in post-mitotic versus dividing neuroblastoma cells driven by an adeno-associated virus vector, Molecular Brain Research, vol. 24(1-4), pp. 27-33, 1994.

* cited by examiner

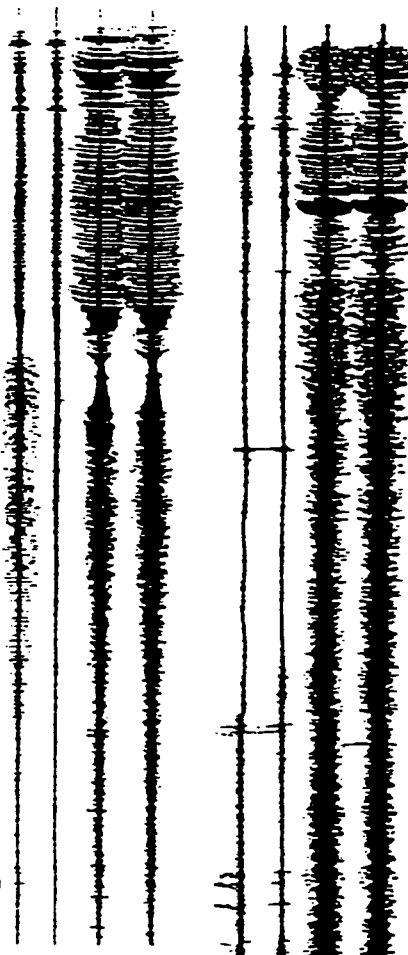
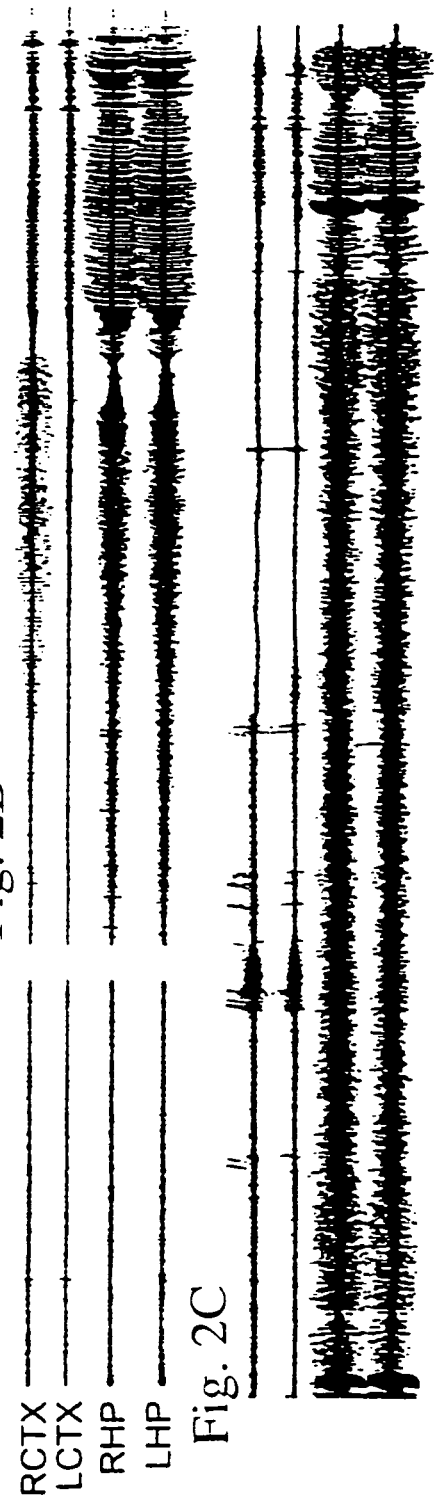
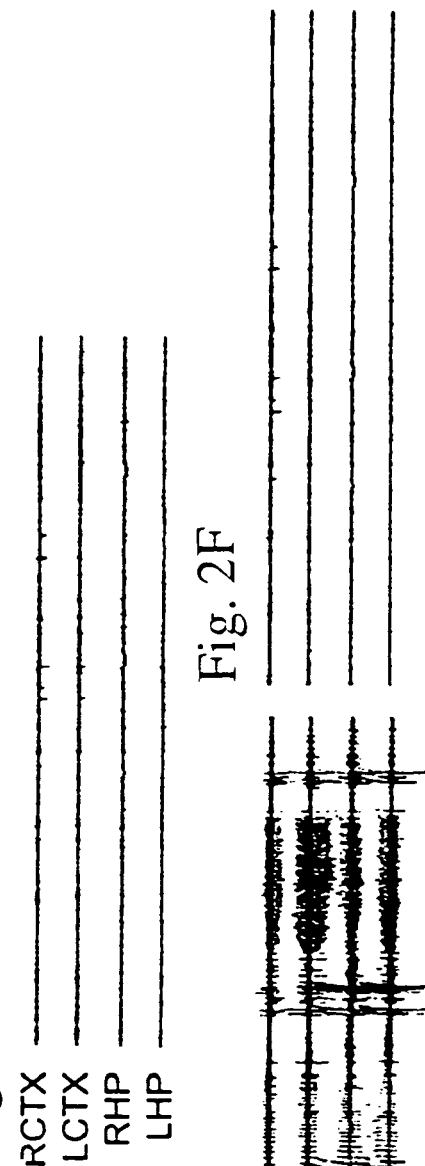
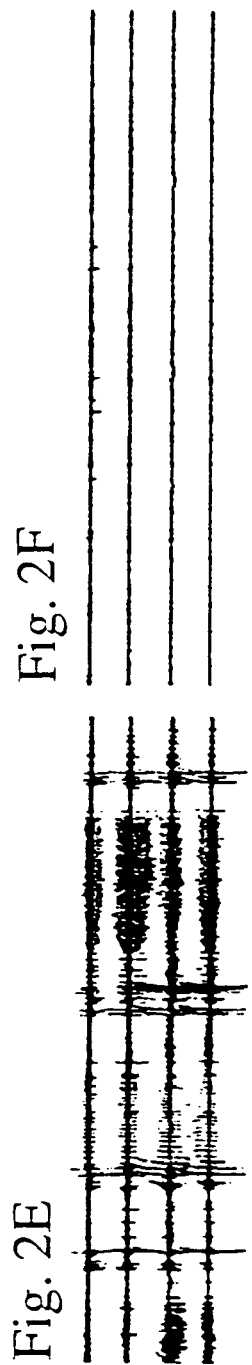
Fig. 2A  Fig. 2B  Fig. 2C  rAAV-NSE-Empty
Fig. 2D  Fig. 2E  Fig. 2F  rAAV-NSE-NPY
RCTX
LCTX
RHP
LHP

Fig. 3A

Nucleic acid sequence of human neuropeptide Y (SEQ ID NO: 1).

```
  1 accccatccg ctggctctca ccccrcggag acgctcgccc gacagcatag tacttgccgc
 61 ccagccacgc ccgcgcgcca gccaccatgc taggtaacaa gcgactgggg ctgtccggac
121 tgaccctcgc cctgtccctg ctcgtgtgcc tgggtgcgct ggccgaggcg taccccrcca
181 agccggacaa cccgggcgag gacgcaccag cggaggacat ggccagatac tactcggcgc
241 tgcgacacta catcaacctc atcaccaggc agagatatgg aaaacgatcc agcccagaga
301 cactgatttc agacctcttg atgagagaaa gcacagaaaa tgttcccaga actcggcttg
361 aagaccctgc aatgtggtga tgggaaatga gacttgctct ctggcctttt cctattttca
421 gcccatattt catcgtgtaa aacgagaatc caccatcct accaatgcat gcagccactg
481 tgctgaattc tgcaatgttt tcctttgtca tcattgtata tatgtgtgtt taaataaagt
541 atcatgcatt c
```

Fig. 3B

Amino acid sequence of human neuropeptide Y (SEQ ID NO: 2).
MLGNKRLGLSGLTLALSLLVCLGALAEAYPSKPDNPGEDAPAEDMARYYSALR
HYINLITRQRYGKRSSPETLISDLLMRESTENVPRTRLEDPAMW

Fig. 4A

Nucleic acid sequence of rhesus monkey neuropeptide Y (SEQ ID NO: 3).

```
  1 gccagccacc atgctaggta gcaagcgact ggggctgtcc ggactgaccc tcgccctgtc
 61 cctgctcgtg tgcctgggtg cgctggccga ggcgtaccct tccaaaccgg acaacccggg
121 cgaggacgcg ccagcggagg acatggccag atactactcg gcgctgcgac actacatcaa
181 cctcatcacc aggcagaggt atggcaaacg atctagccca gagacactga tttcagacct
241 cttgatgaga gaaagcacag aaaatgttcc cagaactcgg cttgaagacc cttcaatgtg
301 gtgatgggaa atgaaacttg ctctctgatc ttttcctatt ttcagcccat atttcatcgt
361 gtaaaatgag agtccaccca tcctaccaat gcatgcagcc actgtgctga a
```

Fig. 4B

Amino acid sequence of rhesus monkey neuropeptide Y (SEQ ID NO: 4).

MLGSKRLGLSGLTLALSLLVCLGALAEAYPSKPDNPGEDAPAED
MARYYSALRHYINLITRQRYGKRSSPETLISDLLMRESTENVPRTRLEDPSMW

Fig. 5A

Nucleic acid sequence of house mouse neuropeptide Y (SEQ ID NO: 5).

```
  1 gtggatctct tctctcacag aggcacccag agcagagcac ccgccgctca gcgacgactg
 61 cccgcccgcc acgatgctag gtaacaagcg aatggggctg tgtggactga ccctcgctct
121 atctctgctc gtgtgtttgg gcattctggc tgaggggtac ccctccaagc cggacaatcc
181 gggcgaggac gcgccagcag aggacatggc cagatactac tccgctctgc gacactacat
241 caatctcatc accagacaga gatatggcaa gagatccagc cctgagacac tgatttcaga
301 cctcttaatg aaggaaagca cagaaaacgc ccccagaaca aggcttgaag acccttccat
361 gtggtgatgg gaaatgaaac ttgttctccc gacttttcca agtttccacc ctcatctcat
421 ctcatcccct gaaaccagtc tgcctgtccc accaatgcat gccaccacta ggctggactc
481 cgccccattt ccctttgttgt tgttgttgta tatatgtgtg tttaaataaa gtaccatgca
541 ttcaaaaaaa aaaaaaaaaa a
```

Fig. 5B

Amino acid sequence of house mouse neuropeptide Y (SEQ ID NO: 6).

MLGNKRMGLCGLTLALSLLVCLGILAEGYPSKPDNPGEDAPAED
MARYYSALRHYINLITRQRYGKRSSPETLISDLLMKESTENAPRTRLEDPSMW

Fig. 6A

Nucleic acid sequence of Norway rat neuropeptide Y (SEQ ID NO: 7).

```
  1 caagctcatt cctcgcagag gcgcccagag cagagcaccc gctgcgcaga gaccacagcc
 61 cgcccgccat gatgctaggt aacaaacgaa tggggctgtg tggactgacc ctcgctctat
121 ccctgctcgt gtgtttgggc attctggctg aggggtaccc ctccaagccg gacaatccgg
181 gcgaggacgc gccagcagag gacatggcca gatactactc cgctctgcga cactacatca
241 atctcatcac cagacagaga tatggcaaga gatccagccc tgagacactg atttcagatc
301 tcttaatgag agaaagcaca gaaaatgccc ccagaacaag gcttgaagac ccttccatgt
361 ggtgatggga aatgaaactt gctctcctga cttttcctag tttccccca catctcatct
421 catcctgtga aaccagtctg cctgtcccac ccaatgcatg ccaccaccag gctggattcc
481 gacccatttc ccttgttgtc gttgtatata tgtgtgttta aataaagtat catgcattc
```

Fig. 6B

Amino acid sequence of Norway rat neuropeptide Y (SEQ ID NO: 8).

MMLGNKRMGLCGLTLALSLLVCLGILAEGYPSKPDNPGEDAPAE
DMARYYSALRHYINLITRQRYGKRSSPETLISDLLMRESTENAPRTRLEDPSMW

Fig. 8A AAV-EMPTY
Fig. 8C
Fig. 8B AAV-NPY
Fig. 8D

METHODS AND COMPOSITIONS FOR THE TREATMENT OF NEUROLOGICAL DISEASE

This application claims priority under 35 USC §119(e) from U.S. Provisional Application Ser. No. 60/573,082 filed May 21, 2004 and U.S. Provisional Application Ser. No. 60/510,985 filed Oct. 14, 2003, each of which is herein specifically incorporated by reference in its entirety.

FIELD OF THE INVENTION

The present invention relates to the delivery of a nucleic acid sequence encoding neuropeptide Y (NPY) or a functional fragment thereof and the expression of NPY or a functional fragment thereof in cells of the nervous system.

BACKGROUND OF THE INVENTION

Several publications and patent documents are referenced in this application in order to more fully describe the state of the art to which this invention pertains. The disclosure of each of these publications and documents is incorporated by reference herein in its entirety.

In general, the invention relates to methods for treating a neurological disease. Neurological diseases/disorders often progress rapidly and can be disruptive of essentially all aspects of a patient's life. As such, these diseases present profound challenges for the patient, care givers, and attending physicians. Moreover, the progressive nature of these diseases makes the passage of time a crucial consideration in the treatment process. Treatment choices for neurological diseases, particularly those affecting cognitive function, can be complicated by the duration of time which is frequently required to determine the efficacy of a therapeutic regimen. Indeed, depending on the disease involved, a significant percent of the population of affected individuals can present with a form of intractable disease.

Methodology directed to human gene therapy renders feasible the treatment of numerous neurological disorders via delivery of nucleic acid sequences directly to the nervous system, wherein their expression can be manipulated in a therapeutically beneficial manner. This is a particularly valuable option for patients with intractable neurological disease, who may, for example, have a form of the disease that is not responsive to the available drugs or may not be able to tolerate the deleterious side effects associated with many therapeutic modalities. Gene transfer into the central nervous system (CNS) is, however, impeded by several features of the system, including the largely post-mitotic nature of most neurons in the brain, constraints related to accessibility into various brain regions, and obstacles pertaining to the blood-brain-barrier.

Retroviral vectors, which are routinely used for somatic cell gene transfer, are not generally useful for applications in post-mitotic neural cells because retrovirally mediated gene transfer requires at least one cell division for integration and expression. To address the challenges inherent to gene transfer into the CNS, a number of vectors and non-viral methods have been developed. A number of studies have achieved varying degrees of success for gene transfer into the CNS using either an ex vivo approach, involving transplantation of cells retrovirally-transduced in vitro, or an in vivo approach. Investigators have also utilized HSV-1 and adenoviral vectors, as well as non-viral methods including cationic lipid mediated transfection to achieve gene transfer into cells of the CNS (Wolff (1993) Curr. Opin. Biol. 3:743-748).

Groves et al., for example, used an ex vivo approach to infect oligodendrocytes with retroviral vectors, which were subsequently transplanted into a syngeneic rat model for a demyelinating disorder (Groves et al (1993) Nature 362:453-457). Non-neuronal cells, including fibroblasts and primary muscle cells, have also been used successfully to introduce exogenous nucleic acid sequences and their encoded products into the CNS (Horrelou et al (1990) Neuron 5:393-402; Jiao et al (1993) Nature 362:450-453).

In vivo approaches have been largely directed to the use of the neurotropic Herpes Simplex Virus (HSV-1) and a number of adenoviral vectors, which have been shown to drive persistent expression (i.e., two months) of marker genes in the rat brain (Davidson et al (1993) Nature Genetics 3:219-2223). In addition to viral vector approaches, other investigators have used direct injection of a cationic liposome:plasmid complex and have demonstrated low level and transient expression of a marker gene using this approach (Ono et al (1990) Neurosci. Lett. 117:259-263).

There have, however, been very few studies directed to introducing "therapeutic" genes into cells of the CNS. The majority of these studies used an ex vivo approach involving transduction of fibroblasts and muscle cells with the human tyrosine hydroxylase gene, which provided a source of L-dopa-secreting cells for use in models of Parkinson's Disease (e.g., Horrelou et al (1990) Neuron 5:393-402; Jiao et al (1993) Nature 362:450-453). HSV vectors have been used for a number of ill vivo approaches involving expression of β-glucuronidase (Wolfe et al (1992) Nature Genetics 1:379-384), glucose transporter (Ho et al (1993) Proc. Natl. Acad. Sci. 90:6791-6795) and nerve growth factor (Federoff et al (1992) Proc. Natl. Acad. Sci. 89:1636-1640). An adenoviral vector has also been used successfully to induce low level transient expression of human α1-antitrypsin (Bajoccchi et al (1993) 3:229-234).

Very few clinical studies documenting gene transfer into the brain have been reported. Of these, Culver et al. [(1992) Science 256:18550-18522] essentially cured rats following the intracerebral implantation of glioma cell lines infected with a retrovirus expressing the HSV-1 thymidine kinase (tk) gene, which were subsequently treated with ganciclovir. The success achieved in the animal model led to approval of a human protocol for glioblastoma multiforme using the retroviral tk vector—ganciclovir approach (Oldfield et al (1993) Human Gene Ther. 4:39-69).

SUMMARY

The present invention is directed to a method for delivering a nucleic acid sequence to a mammalian nervous system target cell, wherein said nucleic acid sequence is expressible in the target cell for greater than three months, said method comprising administering an expression vector to the target cell, wherein said expression vector comprises a nucleic acid sequence encoding NPY, or a derivative or functional fragment thereof.

In an aspect of the method of the invention, the nucleic acid sequence encoding NPY, or a functional fragment thereof, is expressed in a target cell either constitutively or under regulatable conditions.

In an embodiment of the method of the invention, expression of NPY, or a derivative or functional fragment thereof, in a target cell alters neuronal excitability. In another embodiment of the method, expression of NPY, or a derivative or functional fragment thereof, in a target cell reduces neuronal excitability. In yet another embodiment of the method, expression of NPY, or a derivative or functional fragment thereof, in a target cell reduces symptoms associated with neuronal hyperexcitability.

In accordance with the method of the invention, an expression vector is a viral or a non-viral expression vector. Viral expression vectors which may be used advantageously in the method of the invention include, but are not limited to, an adeno associated virus (AAV) vector, a lentivirus vector, an adenovirus vector, and a herpes simplex virus (HSV) vector.

In an aspect of the method wherein the viral expression vector is an AAV vector capable of transducing the target cell, the AAV vector is free of both wildtype and helper virus. Exemplary types of AAV vectors useful in the present invention include serotype 2 AAV vectors and chimeric serotype 1/2 AAV vectors.

In an aspect of the present method, wherein the nucleic acid sequence encoding NPY, or a derivative or functional fragment thereof, is operably linked to an inducible regulatory sequence, activation of the inducible regulatory sequence effects transcription of messenger RNA encoding NPY from the nucleic acid sequence. In an embodiment, an inducible regulatory sequence renders NPY expression nervous system-specific or central nervous system-specific. For some applications, NPY expression is specific to a medial temporal lobe or temporal cortex of the central nervous system. In a further aspect, NPY expression may be directed to the medial temporal lobe, wherein it is localized to the hippocampus and/or amygdala.

In one aspect of the method, NPY expression is neural or glial specific.

In another aspect of the present method, the target cell is a mammalian cell of a mammalian order selected from the group consisting of Primata, Rodenta, Carnivora and Arteriodactyla. More particularly, the target cell may be a human cell. A target cell may exist in a cell culture or within a living mammal.

In an embodiment of the method, an expression vector of the invention is delivered to essentially all nervous system cells of the mammal. Alternatively, an expression vector is specifically delivered to particular cell types or regions of the nervous system of the mammal.

In an aspect of the method, delivering nucleic acid sequences encoding NPY to cells of the nervous system to effect expression of NPY in cells of the nervous system treats a disorder of the nervous system. Nervous system disorders treatable using the method of the invention, include, but are not limited to, epilepsy. Particular examples of epilepsy treatable by the present methods include, but are not limited to, intractable epilepsy and temporal lobe epilepsy.

In accordance with the method of the invention, a nucleic acid sequence encoding NPY is a nucleic acid sequence encoding an amino acid sequence comprising SEQ ID NO: 2; SEQ ID NO: 4; SEQ ID NO: 6; or SEQ ID NO: 8, or a derivative or functional fragment thereof.

In an embodiment of the present method, a nucleic acid sequence encoding NPY is a nucleic acid sequence encoding an amino acid sequence comprising SEQ ID NO: 2, SEQ ID NO: 4, SEQ ID NO: 6, or SEQ ID NO: 8, or a derivative or functional fragment thereof, or an amino acid sequence at least 90% homologous to SEQ ID NO: 2, SEQ ID NO: 4, SEQ ID NO: 6, or SEQ ID NO: 8, or a derivative or functional fragment thereof. In a further aspect of the method, a nucleic acid sequence encoding NPY is a nucleic acid sequence encoding an amino acid sequence comprising SEQ ID NO: 2, SEQ ID NO: 4, SEQ ID NO: 6, or SEQ ID NO: 8, or a derivative or functional fragment thereof, or an amino acid sequence at least 85% homologous to SEQ ID NO: 2, SEQ ID NO: 4, SEQ ID NO: 6, or SEQ ID NO: 8, or a derivative or functional fragment thereof.

In another aspect of the method, a nucleic acid sequence encoding NPY is a nucleic acid sequence comprising SEQ ID NO: 1; SEQ ID NO: 3; SEQ ID NO: 5; or SEQ ID NO: 7; or a derivative or functional fragment thereof.

In another aspect of the method, a nucleic acid sequence encoding NPY is a nucleic acid sequence comprising SEQ ID NO: 1, SEQ ID NO: 3, SEQ ID NO: 5, or SEQ ID NO: 7, or a derivative or functional fragment thereof, or a nucleic acid sequence at least 90% homologous to SEQ ID NO: 1, SEQ ID NO: 3, SEQ ID NO: 5, or SEQ ID NO: 7, or a derivative or functional fragment thereof. In a further aspect of the method, a nucleic acid sequence encoding NPY is a nucleic acid sequence comprising SEQ ID NO: 1, SEQ ID NO: 3, SEQ ID NO: 5, or SEQ ID NO: 7, or a derivative or functional fragment thereof, or a nucleic acid sequence at least 85% homologous to SEQ ID NO: 1, SEQ ID NO: 3, SEQ ID NO: 5, or SEQ ID NO: 7, or a derivative or functional fragment thereof.

In a particular embodiment of the method, an expression vector comprising a nucleic acid sequence encoding NPY may be administered by stereotaxic microinjection.

Also encompassed by the present invention is an AAV vector which retains only the replication and packaging signals of AAV, and which comprises a nucleic acid sequence encoding NPY, or a derivative or functional fragment thereof. A nucleic acid sequence encoding NPY may, for example, comprise a nucleic acid sequence of SEQ ID NO: 1; SEQ ID NO: 3; SEQ ID NO: 5; or SEQ ID NO: 7; or a derivative or functional fragment thereof. A nucleic acid sequence encoding NPY may comprise a nucleic acid sequence encoding an amino acid sequence comprising SEQ ID NO: 2; SEQ ID NO: 4; SEQ ID NO: 6; or SEQ ID NO: 8; or a derivative or functional fragment thereof.

The present invention also includes a composition comprising an AAV vector comprising nucleic acid sequences encoding NPY, or derivative or a functional fragment thereof, and a pharmaceutically acceptable carrier or excipient.

The present invention is also directed to a method for treating a mammal with a neurological disease, said method comprising administering an expression vector to a target cell in the mammal, wherein said expression vector comprises a nucleic acid sequence encoding NPY, or a derivative or functional fragment thereof, and wherein said administering results in expression of NPY, or a derivative or functional fragment thereof, in said target cell and NPY expression reduces the symptoms of the neurological disease, thereby treating the mammal with the neurological disease. In an aspect of the method, the expression vector may be a viral or a non-viral expression vector. In aspects of the method wherein viral vectors are utilized, such vectors include, but are not limited to, an adeno-associated virus (AAV) vector, a lentivirus vector, an adenovirus vector, or a herpes simplex virus (HSV) vector.

In an embodiment of the method, a nucleic acid sequence encoding NPY is a nucleic acid sequence encoding an amino acid sequence comprising SEQ ID NO: 2 or SEQ ID NO: 4, or a derivative or functional fragment thereof. In another embodiment, a nucleic acid sequence encoding NPY is a nucleic acid sequence comprising SEQ ID NO: 1 or SEQ ID NO: 3, or a derivative or functional fragment thereof.

In another embodiment of the method, a nucleic acid sequence encoding NPY is a nucleic acid sequence comprising SEQ ID NO: 1 or SEQ ID NO: 3, or derivative or a functional fragment thereof, or a nucleic acid sequence at least 90% homologous to SEQ ID NO: 1 or SEQ ID NO: 3, or a derivative or functional fragment thereof. The method also encompasses use of a nucleic acid sequence encoding NPY, wherein the nucleic acid sequence comprises SEQ ID NO: 1 or SEQ ID NO: 3, or a derivative or functional fragment thereof, or a nucleic acid sequence at least 85% homologous to SEQ ID NO: 1 or SEQ ID NO: 3.

Neurological diseases treatable using the method of the present invention, include, but are not limited to epilepsy. In specific embodiments, the epilepsy to be treated is intractable epilepsy or temporal lobe epilepsy.

In accordance with the method, an expression vector comprising NPY encoding nucleic acid sequences is administered by stereotaxic microinjection to effect treatment of a mammal with a neurological disease. In one aspect, stereotaxic microinjection is targeted to a medial temporal lobe or temporal cortex of the central nervous system. In a further aspect, administering to the medial temporal lobe may be localized to the hippocampus and/or amygdala.

The present invention also encompasses a method for delivering a nucleic acid sequence to a mammalian nervous system target cell, wherein the nucleic acid sequence is expressible in the target cell for greater than three months, the method comprising administering an adeno-associated virus (AAV) vector to the target cell, wherein the vector transduces the target cell; and the AAV vector comprises a nucleic acid sequence encoding an NPY polypeptide or a derivative or functional fragment thereof, and is free of both wildtype and helper virus. Alternatively, and in accordance with the method, a composition of the invention comprising an AAV vector which encodes an NPY polypeptide or a derivative or functional fragment thereof may be administered.

The present invention also includes a method for treating a mammal with a neurological disease, the method comprising administering an AAV vector to a target cell in the mammal, wherein the AAV vector comprises a nucleic acid sequence encoding an NPY polypeptide or a derivative or functional fragment thereof, and wherein the administering results in expression of NPY, or a derivative or functional fragment thereof, in the target cell and NPY expression reduces the symptoms of the neurological disease, thereby treating the mammal with the neurological disease. In accordance with the method, a composition of the invention comprising an AAV vector which encodes an NPY polypeptide or a derivative or functional fragment thereof may also be administered to effect NPY expression, the expression of which reduces the symptoms of the neurological disease, and thereby treats the mammal with the neurological disease. With regard to epilepsy, for example, symptoms associated with the disease include epileptic seizures and reduction of disease symptoms may refer to a reduction in the frequency, severity, and/or duration of epileptic seizures.

BRIEF DESCRIPTION OF THE DRAWINGS

FIGS. 2A-2F show EEG tracings depicting seizure activity induced by 250 ng intracerebroventricular kainic acid in rats injected 8 weeks before with rAAV-NSE-NPY serotype 2 (D, F) or empty vector (A-C). FIGS. 2A and 2D represent baseline recordings in right (R) and left (L) cortex (CTX) or hippocampi (HP). Traces shown in FIGS. B and C depict discrete and prolonged seizure episodes, respectively, in empty vector-injected rats. Note that only discrete seizure episodes were observed in rAAV-NSE-NPY injected rats (FIG. 2E). Bar=5 sec.

FIGS. 3A and B present (A) a nucleic acid sequence encoding human neuropeptide Y cDNA (SEQ ID NO: 1) and (B) an amino acid sequence of human NPY (SEQ ID NO: 2) encoded by SEQ ID NO: 1.

FIGS. 4A and B present (A) a nucleic acid sequence encoding rhesus monkey neuropeptide Y cDNA (SEQ ID NO: 3) and (B) an amino acid sequence of rhesus monkey NPY (SEQ ID NO: 4) encoded by SEQ ID NO: 3.

FIGS. 5A and B present (A) a nucleic acid sequence encoding mouse neuropeptide Y cDNA (SEQ ID NO: 5) and (B) an amino acid sequence of mouse NPY (SEQ ID NO: 6) encoded by SEQ ID NO: 5.

FIGS. 6A and B present (A) a nucleic acid sequence encoding rat neuropeptide Y cDNA (SEQ ID NO: 7) and (B) an amino acid sequence of rat NPY (SEQ ID NO: 8) encoded by SEQ ID NO: 7.

FIGS. 8A-D show photographs of brain slices revealing expression levels of Y1 and Y2 NPY receptor subtypes.

DETAILED DESCRIPTION OF THE INVENTION

Definitions

Figure 1:
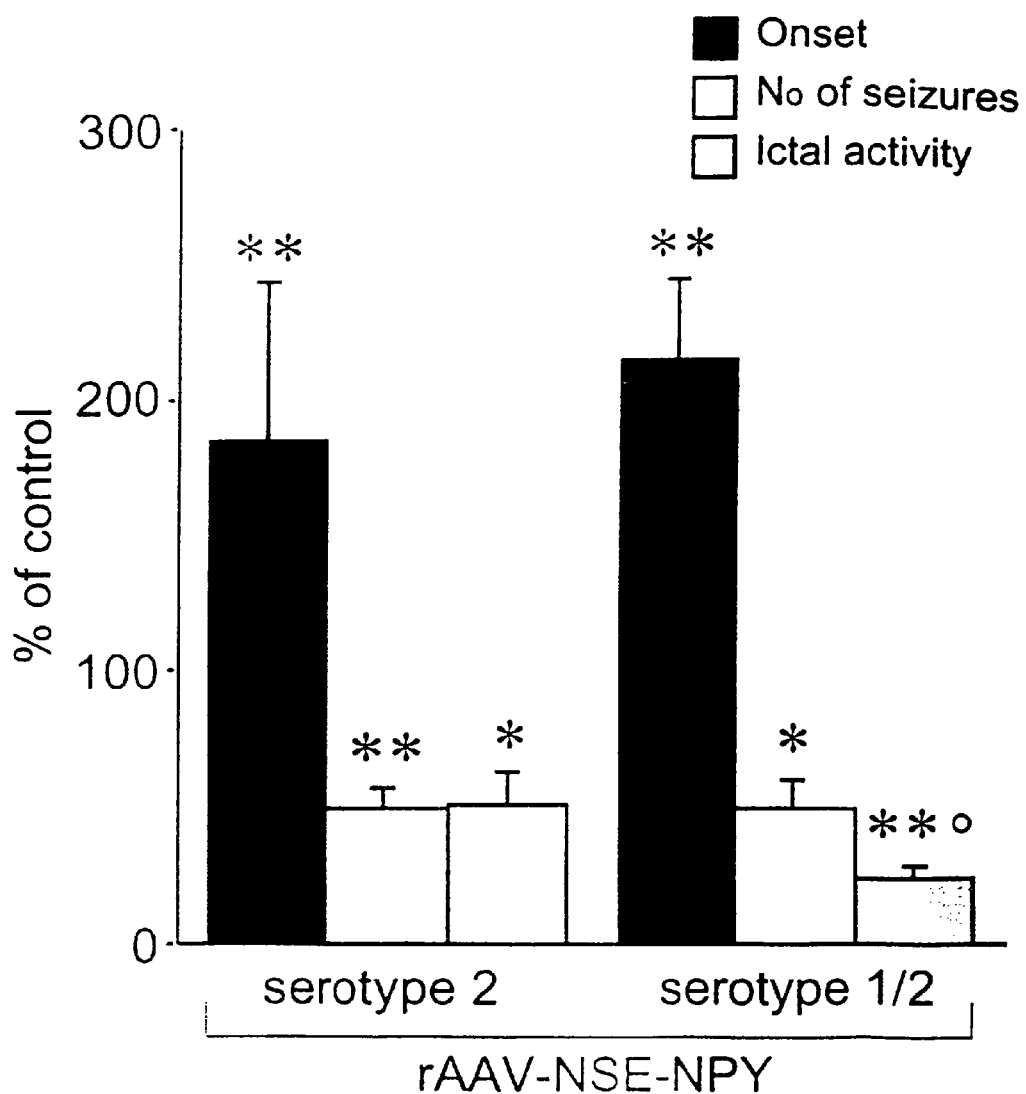
FIG. 1 shows a histogram depicting the mean±SE (n=5-10) number of seizures, time spent in seizures (ictal activity) and time to onset of first seizure expressed as a % of values determined for respective controls (rats injected with rAAV-NSE-Empty). Rats were injected bilaterally into the dorsal hippocampus with the respective vectors and seizures were induced 8 weeks later by unilateral intrahippocampal application of 40 ng kainic acid. *$p<0.05$; **$p<0.01$ vs respective controls; °$p<0.05$ vs serotype 2 by Tukey's test.

Various terms relating to the molecules and methods of the present invention are used hereinabove and also throughout the specifications and claims.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

A "vector" is a replicon, such as plasmid, phage, cosmid, or virus into which another nucleic acid segment may be operably inserted so as to bring about the replication or expression of the segment.

An "expression vector" is a vector which (due to the presence of appropriate transcriptional and/or translational control sequences) is capable of expressing a DNA molecule which has been cloned into the vector and of thereby producing an RNA or protein product encoded by an expressible gene provided by said DNA. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, when a eukaryotic expression vector is employed, e.g., for genetic manipulation prior to gene delivery, then the appropriate host cell would be any eukaryotic cell capable of expressing the cloned sequences.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like. The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on to or inherited by progeny cells or organisms of the recipient cell or organism. In other applications, the introduced nucleic acid may exist in the recipient cell or host organism only transiently.

The term "substantially pure" refers to a preparation comprising at least 50-60% by weight of the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The term "immune response" refers to a physiological response of a subject which is triggered by an antigen or antigenic agent, whereby the humoral branch (relating generally to activation of B cells and the generation of immunologically specific antibodies) and/or the cellular branch (pertaining generally to T cell mediated responses) of the immune system are activated.

As used herein, the terms "reporter," "reporter system", "reporter gene," or "reporter gene product" shall mean an operative genetic system in which a nucleic acid comprises a gene that encodes a product which when expressed produces a reporter signal that is readily measurable, e.g., by biological assay, immunoassay, radioimmunoassay, or by colorimetric, fluorogenic, chemiluminescent or other method. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, and may include, but not be limited to, such elements as promoters, enhancers, translational control sequences, polyA addition signals, transcriptional termination signals and the like.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (at http://www.ncbi.nim.nih.gov/blast/; Altschul et al., 1990, J Mol Biol 215:403-410) using a gapped alignment with default parameters, may be used to determine the level of identity and homology between nucleic acid sequences and amino acid sequences.

The term "functional" as used herein implies that the nucleic or amino acid sequence is functional for the recited assay or purpose.

The term "functional fragment" as used herein refers to a portion or sub domain of polypeptide or peptide that retains an activity of the full length polypeptide or peptide. With respect to NPY, a functional fragment of NPY is a portion or sub domain of an NPY peptide that retains an activity of NPY. In the context of the present invention, an activity of NPY may refer, as described herein, to the ability of NPY to ameliorate symptoms associated with a neurological disorder.

Functional fragments/derivatives of NPY that are useful in the method of the present invention include any NPY functional fragment/derivative that is capable of binding to an NPY receptor. NPY functional fragments/derivatives that are of particular utility in the context of the present invention include those capable of acting as agonists for the Y2 subtype of NPY receptors, which are inhibitory and, in large part, mediate the anti-epileptic and inhibitory effects of NPY. An exemplary NPY functional fragment/derivative capable of acting as a Y2 receptor agonist is C2-NPY.

Particular functional fragments include, but are not limited to various carboxy terminal (C-terminal) fragments of NPY. Exemplary C-terminal fragments of NPY include, without limitation, NPY2-36, NPY13-36, NPY16-36, and NPY18-36. Of these C-terminal fragments, C-terminal NPY fragments that can act as NPY Y2 receptor agonists are of particular utility in the methods of the present invention. Exemplary C-terminal NPY fragments that are capable of acting as agonists for NPY receptors of the Y2 subtype include, but are not limited to NPY13-36 and NPY18-36. See Bleakman et al. (Br. J. Pharmacol 1991, 103:1781-89); Michel et al. (Trends in Pharmacological Sciences 1991, 12:389-394); Kaga et al. (Peptides 2001, 22:501-506); Sun et al. (J Physiol 2001, 531:67-79); Balasubramaniam et al. (Am J Surg 2002, 183:430-4); and D'Angelo et al. (Neuroscience 2004, 125:1-39-1049).

DESCRIPTION OF THE INVENTION

The present inventors have made the novel discovery that long-lasting, localized overexpression of NPY following local application of a recombinant expression vector comprising nucleic acid sequences encoding NPY dramatically reduces acute kainate seizures and kindling epileptogenesis in a rat model system of human epilepsy. As described herein, an exemplary expression vector of the invention is a recombinant adeno-associated viral (AAV) vector. Specifically, EEG seizures induced by intrahippocampal kainate were reduced by 50% to 75% depending on the spread of NPY expression, and seizure onset was markedly delayed. Moreover, status epilepticus was abolished and kindling acquisition was significantly delayed when NPY was expressed by a chimeric AAV vector. Thus, targeted NPY gene transfer represents a novel strategy for effective anti-epileptic treatment of epileptic patients, particularly for drug-resistant epileptic patients.

The method of the present invention is based on the novel finding that focal delivery of nucleic acid sequences encoding NPY using an AAV vector and the resultant localized expression of NPY comprises an effective method for treating epileptic patients. As described herein, focal delivery is preferably directed to the medial temporal lobe (e.g., the hippocampus and amygdala) and/or the temporal cortex. The present inventors have made the surprising discovery that expression of NPY in approximately only 0.1% of the cells in the brain of a rat results in a dramatic reduction in the number of seizures, inhibits prolonged seizure episodes, and generally acts as an anticonvulsant and antiepileptogenic agent. The unexpected nature of the discovery is also underscored by an appreciation that the method of the present invention effects localized expression of NPY in cells that do not normally express NPY. Thus, the ectopic expression of NPY in only about 0.1% of the cells in the brain confers therapeutic benefit to a subject afflicted with a neurological disorder characterized by seizures, such as epilepsy.

The present inventors have also demonstrated that ectopically expressed NPY is appropriately processed from pre-NPY mRNA and, furthermore, that mature NPY is stored properly and then released in response to physiologically relevant cellular stimuli (e.g., a depolarizing stimulus) that normally result in endogenous NPY release. Indeed, prior to the discovery of the present inventors, it was not reasonable to predict that cells that do not express endogenous (native) NPY would be capable of implementing any of the above steps required for the generation of ectopic NPY. In view of the complexity of the above-described processes involved in the synthesis and release of NPY, therefore, the favorable outcome of the method of the present invention would not have been predicted with assurance.

The stereotactic delivery of clinical-grade AAV vectors comprising nucleic acid sequences encoding NPY, or a functional fragment thereof, directly to the seizure focus of an epileptic patient, therefore inhibits and/or dampens seizures by increasing the basal inhibitory tone in the hippocampus. This is a particularly attractive therapeutic option for patients with intractable temporal lobe epilepsy (TLE). The method of the present invention, therefore, provides an alternative to surgical resection of the affected brain area or a delay in the necessity of surgery.

In accordance with the method of the present invention, any gene delivery vector or vehicle can be used, so long as efficient gene transfer to the target cell(s) occurs. Thus, the present methods are not limited to AAV vectors, but rather encompass essentially any viral or non-viral vector. Similarly, naked DNA, DNA-coated particles, liposome encapsulated DNA, or poly-lysine complexed DNA can also be used in the practice of the invention. Viral vectors of utility include, adenovirus (both partially and completely deleted), herpes (HSV) vectors (both partially and completely deleted), and retroviral vectors (e.g., lentiviral vectors), in addition to AAV vectors. For a review of these vectors see Robbins et al. [(1998) Trends Biotechnol 16, 35-40].

NPY, a 36 amino-acid polypeptide, is widely distributed in the CNS where it is involved in various physiological functions [Mitchell et al. *Neuropathol. Appl. Neurobiol.* 23, 299-306 (1997); Pedrazzini et al. *Cell. Mol. Life Sci.* 60, 350-77 (2003)]. NPY has recently become the focus of much attention for its possible involvement in epilepsy [Redrobe et al. *Brain Res.* 848, 153-66 (1999); Vezzani et al. *Trends Neurosci.* 22, 25-30 (1999)]. Despite its widespread distribution in the brain, changes in NPY and its receptors occur in brain regions crucially involved in initiation and propagation of seizures. In rodents, seizures enhance NPY levels in hilar inhibitory hippocampal interneurons, where this peptide is constitutively expressed, and in the excitatory granule cells and their mossy fibers that do not normally express NPY [Marksteiner et al. *Neurosci. Lett.* 112, 143-8 (1990); for review see Vezzani et al. *Trends Neurosci.* 22, 25-30 (1999)]. In the hippocampus of patients with intractable temporal lobe epilepsy (TLE), NPY overexpressing interneurons sprout into terminal areas of excitatory perforant path axons and mossy fiber terminals [de Lanerolle et al. *Brain Res.* 495, 387-95 (1989); Mathern et al. *J. Neurosci.* 15, 3990-4004 (1995); Furtinger et al. *J. Neurosci.* 21, 5804-12 (2001)].

These plastic changes are thought to confer inhibitory effects on neuronal excitability and consequently on seizures. Thus, NPY overexpression in hippocampal GABA-containing interneurons may lead to increased inhibitory input onto terminals of pyramidal neurons and granule cells [Milner et al. *J. Comp. Neurol.* 386, 46-59 (1997)]. This action is likely mediated by presynaptic NPY-Y2 receptors inhibiting glutamate release [Colmers and Bleakman. *Trends Neurosci.* 17, 373-9 (1994); Greber et al. *Br. J. Pharmacol.* 113, 737-40 (1994)]. Indeed, Y2 receptors are upregulated at these sites in epileptic tissue isolated from experimental models and TLE patients [Furtinger et al. *J. Neurosci.* 21, 5804-12 (2001); for review see Vezzani et al. *Trends Neurosci.* 22, 25-30 (1999)].

An anticonvulsant role for NPY has been suggested experimentally as demonstrated by responses following exogenous application of NPY or endogenous NPY release. Transgenic rats overexpressing NPY, for example, exhibit reduced seizure susceptibility and epileptogenesis [Vezzani et al. *Neuroscience* 110, 237-43 (2002)], whereas knock-out mice lacking NPY or the Y2 receptor gene are more vulnerable to chemically- or electrically-induced convulsions [Baraban et al. *J. Neurosci.* 17, 8927-36 (1997); DePrato Primeaux et al. *Neurosci. Lett.* 287, 61-4 (2000); Weinshenker et al. *J. Neurosci.* 21, 7764-9 (2001); El Bahh et al., No 148.12. Soc for Neurosci, 2002). In hippocampal slices from epileptic patients with hippocampal seizure onset, NPY has a potent and long-lasting inhibitory action on perforant path-evoked excitatory responses from dentate granule cells [Patrylo et al. *J. Neurophysiol.* 82, 478-83 (1999)].

Neurological Disease

The incidence of neurological disease worldwide is on the rise, in part due to the relative increase in the elderly population. In view of the prevalence of neurological disease in the human population and the devastating effects many of these conditions have on the physical, intellectual, and emotional well being of a patient, developing new and improved therapeutic regimens for treating patients afflicted with such diseases is of paramount importance. Since epilepsy, for example, affects over fifty million people worldwide, developing more effective therapeutics for this neurological disease is a global concern. Underscoring the dire need for anti-epileptic therapeutics is the devastatingly high frequency of epileptics (estimated to be approximately 30-40% of affected individuals) who are refractive to the available therapeutics. Such patients are generally characterized as having intractable disease.

The present invention relates particularly to a method for treating patients with epilepsy, particularly intractable epilepsy. Medically intractable epilepsy has been defined as persistent seizure activity, which, despite maximal medical treatment, remains sufficiently debilitating to warrant the risks of surgery. As described below, this definition has different meanings in pediatric and adult epilepsy populations.

Adults often have a low frequency of seizures, so it is not uncommon for adults to be diagnosed with intractable epilepsy, even at a frequency of only one seizure a month. As a result, the assessment process in these patients often involves a prolonged process wherein patient response to different medications and doses are evaluated in both mono- and polytherapy.

In contrast, certain pediatric seizure syndromes are uniquely defined by their seizure intractability, (e.g.) congenital malformations such as hemimeganencephaly, Sturge-Weber syndrome, or Rasmussen's encephalitis. It is not unusual for such pediatric patients to undergo 40-100 seizures a day, despite maximal medical therapy. Medical regimens for these conditions often fail, demonstrating poor responses to first- and second-line medications, as well as to polytherapy. Because of the high frequency of seizures, trials of therapeutic regimens can be tested in an expeditious manner, thereby facilitating an accurate assessment of the best mode for treatment.

Many factors may predispose a child to the development of seizures and epilepsy, including: genetic and congenital malformations, intrauterine and postnatal insults, anoxic injuries, infections (viral and bacterial), and vascular malformations and compromise due to, for example, ischemia, trauma, and tumors.

Intractable epilepsy is broadly characterized by 1) a high incidence of partial seizure followed by a generalized seizure (particularly in temporal lobe epilepsy); 2) a high incidence of symptomatic epilepsy caused by an organic lesion in the brain; 3) a long duration time between onset of disease and diagnosis, and a high frequency of seizures; and 4) a high incidence of status epilepticus in the case history. The features of intractable epilepsy suggest that the temporal lobe is of particular significance in the etiology of intractable epilepsy. Moreover, as epilepsy progresses in a patient, it can evolve to become intractable. Intractable epilepsy may also present clinically following trauma, brain surgery, or relapse following surgery for epilepsy.

Intractable epilepsy is categorized into three clinical types, including: localization-related epilepsies and syndromes, generalized epilepsies and syndromes, and indeterminate epilepsies and syndromes, whether focal or generalized.

Examples of localization-related epilepsies and syndromes include temporal lobe epilepsies, frontal lobe epilepsies, and multi-lobe epilepsies. Temporal lobe epilepsies and frontal lobe epilepsies are typical examples of intractable epilepsy. Multi-lobe epilepsies are thought to involve two or more lobes. Examples of generalized epilepsies and syndromes include Lennox-Gastaut syndrome, West syndrome, and myoclonic epilepsy. An example of indeterminate epilepsies and syndromes, whether focal or generalized, is severe myoclonic epilepsy in infancy, which exhibits a variety of seizure types. In particular, tonic-clonic seizures occur frequently, which often lead to status epilepticus. In view of the severity of such conditions, treatment at early age by a medical practitioner who specializes in epilepsy is essential to the well being of the patient.

Seizures associated with intractable epilepsy have been classified into categories, which include, but are not limited to, tonic seizures, tonic-clonic seizures, atypical absence seizures, atonic seizures, myoclonic seizures, clonic seizures, simple partial seizures, complex partial seizures, and secondary generalized seizures.

Temporal lobe epilepsy is a type of intractable epilepsy characterized by a seizure focus in the temporal lobe. It is categorized with symptomatic and localization-related epilepsies, which also include frontal lobe epilepsies, parietal lobe epilepsies, and occipital lobe epilepsies, based on the international classification of epilepsy. The syndromes of temporal lobe epilepsy vary in accordance with the locale of the seizure focus and the type of seizure propagation. Of note in this regard, the temporal lobe has an anatomically complex structure including the neocortex, allocortex, and paleocortex. Temporal lobe epilepsy generally causes complex partial seizures, but may also induce simple partial seizures, secondary generalized seizures, and combinations thereof.

Simple partial seizures include autonomic and mental symptoms, as well as sensory symptoms involving olfaction, audition, or vision. Complex partial seizures often exhibit motion stopping followed by eating-function automatism, and are divided into amygdala-hippocampus seizures and lateral temporal lobe seizures according to localization. In the case of temporal lobe epilepsy, 70-80% of the seizures are localized to the hippocampus, in which aura, motion stopping, lip automatism, and clouding of consciousness are successively developed to result in amnesia. When the focus is in the amygdala, autonomic symptoms such as dysphoria in the epigastrium, phobia, and olfactory hallucination may result. Lateral temporal lobe seizures include auditory illusion, hallucination, and speech disturbance when the focus is in the dominant hemisphere. Temporal lobe epilepsy exhibits a long-term psychosis-like state in addition to other symptoms and recognition-and-memory disorder more frequently than do other epilepsies. Treatment of temporal lobe epilepsy has routinely been directed to pharmacotherapy employing of a combination of drugs at maximum tolerated dose or through surgical treatment.

Cortex epilepsy, another type of intractable epilepsy, is associated with a focus in the cerebral cortex, and is classified as a symptomatic epilepsy belonging to localization-related (focal) epilepsies and syndromes. In the international classification, seizures associated with cortex epilepsy are classified as simple partial seizures, in the absence of a reduction in consciousness. Cortex epilepsies are usually caused by a cerebral tumor, an aftereffect of cephalotrauma or a perinatal insult. Based on the focus, cortex epilepsy is classified as temporal lobe epilepsy, parietal lobe epilepsy, or occipital lobe epilepsy.

Traumatic epilepsy is another type of intractable epilepsy. Traumatic epilepsy, in a broad sense, is divided into two categories, "early epilepsy" and "late epilepsy". Early epilepsy is not considered a true epilepsy because it is caused by stimulation of the brain induced by convulsion within a week after suffering a trauma. In contrast, late epilepsy is considered a true epilepsy in that it presents one or more weeks after suffering a trauma.

Most of the traumatic epilepsies are associated with focus formation at the damaged portion of the cortex, and are viewed as typical examples of partial epilepsies. Treatment of traumatic epilepsy is, therefore, directed to pharmacotherapy. Since the onset and progression of symptoms in different individuals are diverse, however, many cases become intractable through administration of an antiepileptic agent.

Secondary generalized seizure is one of the symptoms associated with intractable epilepsy. It is a type of partial seizure, which exhibits a clinical syndrome and an electrocephalogram feature detected as excitation of neurons with initiation of the seizure in a limited portion of one cerebral hemisphere. A secondary generalized seizure is initiated as a simple partial seizure (without impairment of consciousness) or a complex partial seizure (with impairment of consciousness), and develops to general convulsion induced through secondary generalization. The main symptom thereof is a convulsion such as a tonic-clonic seizure, a tonic seizure, or a clonic seizure.

Intractable epilepsy also comprises the symptom of complex partial seizure, a term which refers to a partial seizure with impairment of consciousness. In the international classification draft (1981), the complex partial seizure is defined as a seizure "with impairment of consciousness exhibiting an electrocephalogram during a seizure in which unilateral or bilateral electric discharge attributed to a focus in a diffuse or a temporal or front-temporal portion."

The neuromechanism responsible for complex partial seizure is thought to include the amygdala, hippocampus, hypothalamus, and parolfactory cortex, in addition to the frontal and temporal lobes. The seizures typically last 1-2 minutes or slightly longer, and the onset and cessation of the seizures are not abrupt, but gradual. Examples of complex partial seizures include (1) seizures with reduction of consciousness (gradually evolving impairment of consciousness, arrest of motion, speech, and reaction, and amnesia); (2) cognitive seizures (deja-vu, jamais-vu, ideo-seizures); (3) affective seizures (fear, anger, emptiness, strangeness, delight, joy); (4) psycho-sensory seizures (hallucinations; visual, auditory, gustatory, olfactory, cenesthesia); and (5) psycho-motor seizures (automatism, lip-licking, chewing, stereotypy).

In status epilepticus, another type of intractable epilepsy, consciousness is lost and can not be restored during the course of the seizure. Such seizures can last for 30 or more minutes and can become repetitive. Of note, any type of seizure may evolve to status epilepticus. The most common example of which is a tonic-clonic seizure, and status epilepticus thereof is fatal and must be treated immediately. In many cases, cessation of an antiepileptic agent induces status epilepticus. Thus, an antiepilepitic agent is administered intravenously while the central nervous system disorder and whole-body conditions are monitored and controlled. In that status epilepticus convulsions are known to lead to intractable epilepsy, immediate and appropriate action is required for the diagnosis of and first aid for a status epilepticus convulsion. Suppression of a convulsive seizure at the early stage is an important key to aftercare.

Clinical models for intractable epilepsy in humans have been developed in animal model systems. Examples of such animal models include a "kindling model" and "kainic acid induced seizures".

Kindling Model

When weak electrical stimulation is applied to a particular portion of the brain repeatedly at intervals, evolution of a partial seizure to a generalized seizure is observed. This phenomenon is called kindling. The effect of kindling is long term and results in the formation of an epileptic origin in the brain, which sometimes causes a spontaneous epileptic seizure. Although kindling is a long term phenomenon, large-scale morphological changes in the brain are not observed. Thus, the kindling model serves as a useful experimental model for epilepsy in that non-specific epileptic origin, in the absence of tissue damage, is acquired in the brain and persists for a long time. The availability of this model enables investigation of the potentiation process of acquired epileptic origin relating to intractable epilepsy and of pathologically specific stages such as onset, continuation, and cessation of seizures (e.g., post-seizure stage and seizure-absence stage).

A variety of clinically relevant models of epilepsy can be produced using a kindling model and the desired outcome can be achieved based on the portion of the brain selected for stimulation. The most sensitive portion is the amygdala, which is repeatedly stimulated at an afterdischarge threshold (minimum stimulation intensity; generally once per day), to exhibit seizure stages as follows: Stage 1 (chewing); Stage 2 (head nodding); Stage 3 (forelimb clonus); Stage 4 (rearing); and Stage 5 (rearing and falling). Stages 1 and 2 correspond to a complex partial seizure of human temporal lobe epilepsy, and Stages 3 to 5 are considered to be stages of secondary generalized seizure. Stage 5 is regarded as a stage of establishment of kindling. Once kindling is established, susceptibility to electrical stimulation is maintained essentially for the life of the animal.

Kindling is similar to human epilepsy not only in terms of seizure symptoms but also in responsiveness to therapeutics, such as an antiepileptic agent. Thus, the kindling model is a particularly useful tool for studying epileptic phenomena. Using a kindling model having a focus in the limbic system or the cortex, a variety of phenomena can be investigated, such as, an effect on a partial seizure; an effect on a developmental stage from a partial seizure to a secondary generalized seizure; action mechanisms thereof (such as action for acquisition of epileptogenesis, and neuromechanism relating to generalization of a seizure in the limbic system); and an effect on clinical symptoms. A pharmaceutical effect during a kindling development process toward establishment of a generalized seizure is called "preventive effect," which is evaluated by a preventive effect of a pharmaceutical on acquisition of epileptogenesis. A pharmaceutical effect during a kindling development process involving repeated stimulation after establishment of a generalized seizure is called "therapeutic effect". A kindling model, therefore, is an excellent animal model for treatment-resistant temporal lobe epilepsy with a complex partial seizure, a secondary generalized seizure observed in human patients.

The method of the present invention is directed to the treatment, prevention, alleviation or inhibition of diseases or disorders associated with an altered amount of NPY, NPY receptors and/or altered NPY signaling in a mammal, preferably in a human. These disorders or maladies include: NPY-related cerebral diseases and conditions, such as cerebral infarction, epilepsy, neurodegenerative conditions, stroke and related conditions, cerebral vasospasm or hemorrhage, anxiety, schizophrenia, depression and dementias.

Exogenous DNA

Unless otherwise indicated, the present invention utilizes standard techniques well known to practitioners of molecular biology and described in several laboratory protocol handbooks, including: *Molecular Cloning: A Laboratory Manual*, Sambrook et al. eds., Cold Spring Harbor Laboratory Press (1989); Ausubel et al. eds., *Current Protocols in Molecular Biology*, John Wiley & Sons, NY, N.Y. (1995).

The "exogenous DNA" of the present invention is exogenous with regard to the expression vector (e.g., AAV) and the recipient. See below for additional clarification of this term as it pertains to the recipient. The DNA may be synthetic DNA, complementary DNA, genomic DNA, or a combination thereof. The DNA may be of any sequence or length, provided that it may be incorporated into the vector and delivered to target cells. Typically, because of the packaging limitations of AAV, for example, the exogenous DNA will have a length of about 10-5,000 bases. Preferably, the DNA is 100 to 4,000 bases.

In a particular embodiment, the exogenous DNA is an NPY encoding nucleic acid sequence, such as human NPY cDNA (SEQ ID NO: 1) or monkey NPY cDNA (SEQ ID NO: 3). Alternatively, human or monkey genomic NPY encoding sequences may comprise the exogenous DNA. Nucleic acid sequences encoding functional fragments, derivatives or mutants of human or monkey NPY may comprise the exogenous sequences.

With respect to the present invention, particular functional fragments and/or derivatives of NPY are capable of binding to NPY receptors. Particular functional fragments and/or derivatives of NPY include, but are not limited to: NPY2-36 (amino acid residues 2-36 of full length NPY), NPY13-36 (amino acid residues 13-36 of full length NPY), NPY16-36 (amino acid residues 16-36 of full length NPY), and NPY18-36 (amino acid residues 18-36 of full length NPY) and C2-NPY. NPY13-36, NPY18-36, and C2-NPY may be used to particular advantage in the method of the present invention because these fragments/derivatives are capable of acting as NPY Y2 receptor agonists. As used herein, NPY2-36, NPY13-36, NPY16-36, NPY18-36, or C2-NPY may be fragments/derivatives of full length human, monkey, or rodent NPY polypeptide sequences. Such full length polypeptide sequences include, but are not limited to SEQ ID NO: 2, SEQ ID NO: 4, SEQ ID NO: 6, or SEQ ID NO: 8. Nucleic acid sequences encoding functional fragments and/or derivatives of SEQ ID NO: 2, SEQ ID NO: 4, SEQ ID NO: 6, or SEQ ID NO: 8 are also encompassed by the present invention.

A skilled practitioner would appreciate that a nucleic acid sequence encoding an NPY protein of any species can be used in the method of the present invention. Such NPY proteins are homologous and share common properties relating to activity and function. The human NPY sequence is, for example, 98% homologous to NPY orthologs of non-human primates (e.g. Pan species) and 88% homologous to NPY orthologs of both rat and mouse. NPY sequences isolated from a variety of species are available publicly. See, for example, GenBank Accession Nos. K01911 *[Homo sapiens* (humans)] NPY mRNA; AF162280 [Macaca mulatta (rhesus monkey) NPY mRNA; SEQ ID NO: 3]; BC043012 *[Mus musculus* (house mouse) NPY mRNA; SEQ ID NO: 5]; and NM_012614 *[Rattus norvegicus* (Norway rat) NPY mRNA; SEQ ID NO: 7].

In addition to the nucleic acid sequences presented in SEQ ID NOs: 1, 3, 5, and 7, the method of the invention may also utilize a nucleic acid that is a mutant, variant, or derivative of one of these sequences. A variant sequence may differ by an alteration of one or more of an addition, an insertion, a deletion and a substitution of one or more nucleotides of a particular sequence (e.g., SEQ ID NOs: 1, 3, 5, or 7). Changes to a nucleotide sequence may result in an amino acid change at the protein level, or not, as determined by the genetic code.

Thus, a nucleic acid according to the present invention may include a sequence different from the sequence shown in a SEQ ID NO: of the invention, yet encode a polypeptide with the same amino acid sequence.

On the other hand, the encoded polypeptide may comprise an amino acid sequence which differs by one or more amino acid residues from the amino acid sequences shown in a SEQ ID NO: of the invention (e.g., SEQ ID NOs: 2, 4, 6, or 8). Nucleic acid encoding a polypeptide which is an amino acid sequence mutant, variant, or derivative of a SEQ ID NO: of the invention is further provided by the present invention. Nucleic acid encoding such a polypeptide may show greater than 60% homology with a coding sequence shown in a SEQ ID NO: of the invention, greater than about 70% homology, greater than about 80% homology, greater than about 90% homology or greater than about 95% homology.

As used herein, a nucleic acid sequence encoding a functional fragment, derivative, or mutant of NPY is a nucleic acid sequence that encodes a peptide that retains at least one activity of full length or wild type NPY. Activities ascribed to full length or wild type NPY are known in the art and exemplified herein. Assays for assessing NPY activity are offered in cell-based assays, for example, wherein cells that express endogenous NPY receptor or which have been engineered to express exogenous NPY can be incubated with NPY (e.g., different concentrations of NPY) and downstream signaling responses monitored to measure NPY activity. The Examples of the present invention also provide in vivo assays for measuring/detecting NPY activity.

In a particular embodiment, a nucleic acid sequence encoding a functional fragment, derivative, or mutant of NPY is, for example, a nucleic acid sequence that encodes NPY2-36 (amino acid residues 2-36 of full length NPY), NPY13-36 (amino acid residues 13-36 of full length NPY), NPY16-36 (amino acid residues 16-36 of full length NPY), NPY18-36 (amino acid residues 18-36 of full length NPY), or C2-NPY. As described herein above, functional fragments and/or derivatives of NPY that are capable of acting as agonists for the Y2 subtype of NPY receptors may be used to particular advantage in the method of the present invention. Exemplary functional fragments and/or derivatives of NPY that act as Y2 receptor agonists include, without limitation, NPY13-36, NPY18-36, and C2-NPY. NPY2-36, NPY13-36, NPY16-36, NPY18-36, or C2-NPY may be fragments/derivatives of full length human, monkey, or rodent NPY polypeptide sequences, such as SEQ ID NO: 2, SEQ ID NO: 4, SEQ ID NO: 6, or SEQ ID NO: 8. Exemplary nucleic acid sequences encoding functional fragments and/or derivatives of SEQ ID NO: 2, SEQ ID NO: 4, SEQ ID NO: 6, or SEQ ID NO: 8 include, but are not limited to those that encode a NPY2-36, NPY13-36, NPY16-36, NPY18-36, or a C2-NPY functional fragment/derivative of a full-length NPY polypeptide.

The present invention may be used for gene therapy of any genetically-based or -acquired disorder associated with altered NPY activity or function. In a particular embodiment, the disorder is a neurological disorder associated with or related to NPY activity. An individual may be in need of gene therapy because, as a result of one or more mutations in the regulatory region and/or the coding sequence of one or more genes, a particular gene product is inappropriately expressed, e.g., has an incorrect amino acid sequence, or is expressed in the wrong tissues or at the wrong times, is underexpressed, or overexpressed, or cells which normally express NPY or its receptors are involved in a disease process. Therefore, DNA delivered to that individual (i.e., a recipient) is considered exogenous even if it is identical to a native/endogenous gene, provided it differs in the regulatory or coding region from that of the cognate gene of the individual to whom it is delivered. As a consequence of this difference, such an exogenous gene encodes a different gene product or is expressed to a different degree and/or in different cells, under at least some conditions.

Exemplary Delivery Vectors

Adeno-Associated Virus (AAV) and AAV Vectors

Adeno-Associated Virus (AAV) is a defective parvovirus whose genome is encapsidated as a single-stranded DNA molecule. Strands of plus and minus polarity are both packaged, but in separate viral particles. Although AAV can replicate under special circumstances in the absence of a helper virus, efficient replication generally requires coinfection with a helper virus of the herpesvirus or adenovirus family. In the absence of a helper virus, AAV establishes a latent infection in which the viral genome exists as an integrated provirus in the host cell. Of note, AAV gene expression is not required to establish a latent infection. If a latently infected cell line is subsequently superinfected with a suitable helper virus, the AAV provirus is excised and the virus enters a "productive" phase of its life cycle. It has, however, been reported that certain AAV-derived transducing vectors are not rescued by adenovirus superinfection.

Unlike wild-type adeno-associated virus, which in addition to the terminal inverted repeats, retain rep proteins that enable it to integrate into human chromosome 19 at a specific site, AAV vectors, which are almost invariably rep-deficient, have no known specific or preferred integration site. AAV vectors can integrate into chromosome 19, although not at the wild-type virus integration site. They may also integrate into any of the other human chromosomes. AAV vectors are, however, preferred for most gene therapy applications because the vector genome largely exists as a stable episome, in a variety of forms of tandem concatamers (e.g. head to tail, head to head, tail to tail) as well as monomers and large concatamers, in addition to integrated genomes. Notably, rep, which is required for chromosome 19 targeting, is frequently toxic to a recipient cell and limits the packaging capability of the vector. Hence, rep-deficient AAV vectors are preferred for long-lasting and non-toxic gene transfer to both dividing and non-dividing cells.

Although AAV is a human virus, its host range for lytic growth is unusually broad. Cell lines from virtually every mammalian species tested (including a variety of human, simian, canine, bovine and rodent cell lines) can be productively infected with AAV, provided an appropriate helper virus is used (e.g., canine adenovirus in canine cells). Despite this, no disease has been associated with AAV in either human or other animal populations, unlike both HSV and adenovirus. AAV has, however, been detected as a nonpathogenic coinfecting agent in fecal, ocular and respiratory specimens isolated during acute adenovirus infections. AAV has not been shown to be a coinfective agent associated with any other illnesses.

Likewise, latent AAV infections have been identified in both human and nonhuman cells. Overall, virus integration appears to have no apparent effect on cell growth or morphology. See Samulski (1993) Curr. Op. Gen. Devel. 3:74-80.

The genome of AAV-2 is 4,675 bases in length and is flanked by inverted terminal repeat sequences of 145 bases each. These repeats are believed to act as origins for DNA replication. There are two major open reading frames. The left frame encodes at least four non-structural proteins comprising the Rep group. Two promoters, P5 and P19, control expression of these proteins. Via differential splicing, the P5 promoter drives expression of the Rep 78 and Rep 68 proteins, and the P19 promoter drives expression of the Rep 52 and Rep 40 proteins. The Rep proteins are thought to be involved in viral DNA replication, trans-activation of transcription from the viral promoters, and repression of heterologous enhancers and promoters.

The right ORF, the expression of which is regulated by the P40 promoter, encodes the capsid proteins Vp1 (91 kDa), Vp2 (72 kDa) and Vp3 (60 kDa). Vp3 comprises 80% of the virion structure, while Vp1 and Vp2 are minor components. A polyadenylation site is found at map unit 95. For the complete sequence of the AAV-2 genome, see Vastava et al (1983) J. Virol. 45:555-64.

McLaughlin et al. [(1988) J. Virol. 62:1963-73] prepared two AAV vectors: dl 52-91, which retains the AAV rep genes, and dl 3-94, in which all of the AAV coding sequences have been deleted. It does, however, retain the two 145 base terminal repeats, and an additional 139 bases which include the AAV polyadenylation signal. Restriction sites were introduced on either side of the signal.

A foreign gene, encoding neomycin resistance, was inserted into both vectors. Viral stocks were prepared by complementation with a recombinant AAV genome, which supplied the missing AAV gene products in trans but was too large to be packaged. The virus stocks produced by this method were, however, contaminated with wild type AAV (10% in the case of dl 3-94), presumably as a result of homologous recombination between the defective and the complementing virus.

Samulski et al. [(1989) J. Virol. 63:3822-28] subsequently developed a method for producing recombinant AAV stocks without detectable wild-type helper AAV. Their AAV vector retained only the terminal 191 bases of the AAV chromosome. In the helper AAV, the terminal 191 bases of the AAV chromosome were replaced with adenovirus terminal sequences. Since sequence homology between the vector and the helper AAV was thus essentially eliminated, no detectable wild-type AAV was generated by homologous recombination. Moreover, the helper DNA was not replicated and encapsidated because the AAV termini are required for this process. Thus, helper virus can be completely eliminated from the final product, thereby resulting in a helper-free AAV vector stock.

Evidence of the utility of helper-free AAV vectors for transducing human cells is provided in numerous publications. Muro-Cacho et al. [(1992) J. Immunother. 11:231-237], for example, successfully used AAV-based vectors for gene transfer into both T- and B-lymphocytes. Walsh et al. [(992) Proc. Nat. Acad. Sci. (USA) 89:7257-61] employed an AAV vector to introduce and express a human gamma globulin gene into human erythroleukemia cells. Flothe et al. [(1993) J. Biol. Chem. 268:3781-90] delivered the cystic fibrosis transmembrane conductance regulator gene to airway epithelial cells by means of an AAV vector. See also Flotte et al (1992) Am. J. Respir. Cell. Mol. Biol. 7:349-56; Flotte et al (1993) Proc. Nat. Acad. Sci. (USA) 90:10613-17.

Additional information pertaining to recombinant parvovirus vectors and methods of making such vectors is presented in U.S. Pat. No. 6,491,907. Improved methods for generating helper virus-free AAV stocks are also found in U.S. Pat. No. 6,458,587. The entire contents of each of which is incorporated herein by reference.

As exemplified herein, serotype 2 AAV vector particles display serotype 2 capsid proteins. Whereas chimeric serotype 1/2 vector particles display chimeric capsid proteins comprised of chimeric/hybrid (serotype 1 and 2) capsid proteins.

A number of AAV vectors have been developed (including serotypes 1-9), all of which are derivatives of the adeno-associated virus. See, for example, U.S. Pat. Nos. 6,491,907 and 6,503,888. Although particular AAV vectors are used in the examples presented herein, a skilled practitioner would appreciate that the method of the invention can be practiced with essentially any AAV vector that is capable of effecting long term expression of an exogenous gene (e.g., NPY or a functional derivative or functional fragment thereof) in a cell of the CNS, without causing a clinically unacceptable spectrum of deleterious side effects. AAV vectors of utility in the methods of the present invention are capable of transducing postmitotic cells, such as mature neurons, with high efficiency and stability, while exhibiting minimal immunogenicity and non-pathogenicity. Such AAV vectors may also demonstrate a broad host and cell range.

In a particular embodiment, an AAV vector of the invention is modified to reduce the potential for rescue by complementation with herpesvirus or adenovirus, for example, which may be present in a patient in the absence of clinical symptoms of infection. Such modifications can involve point mutations to one or more viral genes, which either prevent expression of the gene, or result in the expression of a modified, nonfunctional gene product. In that point mutations are reversible, deletion of part or all of the gene in question is preferable. This approach also facilitates the insertion of larger exogenous nucleic acid sequences into the vector, the total size of which is restricted by the capability of the packaging functions to efficiently package a construct into a virus particle.

It is preferable that all of the viral genes be deleted, or otherwise inactivated, as in the AAV vector dl3-94. It should be understood, however, that a vector retaining one or more AAV genes, such as the AAV vector dl52-91, can also be used for gene delivery.

For propagation of the vector in vitro, susceptible cells are co-transfected with the AAV-derived vector and a suitable AAV-derived helper virus or plasmid. Preferably, the vector retains from AAV essentially only the recognition signals for replication and packaging.

The AAV-derived sequences need not correspond exactly to their wild-type prototypes. The AAV vectors of the present invention may, for example, feature mutated inverted terminal repeats, provided that the vector can still be replicated and packaged with the assistance of helper virus, and still establish a nonpathogenic latent infection in target cells.

The vector may further comprise one or more restriction sites into which foreign DNA may be cloned without interfering with packaging and replication. Preferably, at least one unique restriction site is provided. The vector may also comprise one or more marker genes to facilitate genetic manipulation and detection. Suitable marker genes include, but are not limited to, the neomycin and hygromycin resistance genes, bacterial lacZ gene, and the firefly luciferase gene.

AAV-derived Helper Virus or Plasmid

The AAV-derived helper virus or plasmid may be any virus or plasmid that is capable of providing the spectrum of proteins necessary for the replication and packaging of an AAV vector in a suitable host cell, for the purpose of producing vector stock.

In a particular embodiment, the helper virus or plasmid has been engineered to reduce the risk of recombination between the helper DNA and the vector DNA. Most desirably, there is minimal or no sequence homology retained between the AAV sequences of the vector DNA and the AAV sequences of the helper DNA. For example, the helper DNA may be an AAV in which the AAV inverted terminal repeats are replaced by the corresponding sequences of another virus, such as adenovirus (e.g., adenovirus type 5 DNA). See Samulski et al., supra.

Alternatively, in another embodiment, helper adenovirus may be removed by heat inactivation at 56° C. for 30 minutes, or separated from packaged AAV vectors by centrifugation in a cesium chloride gradient.

A skilled artisan would appreciate that any AAV (e.g., sertoypes 1-9 or chimeric viruses thereof) or related parvovirus vector may be used in the methods of the present invention. Indeed, the methods of the present invention are not limited to any particular viral or non-viral vector for delivery of nucleic acid sequences encoding NPY to a target cell in the brain. A skilled practitioner would understand that the method of the invention can be practiced with essentially any vector (viral or non-viral) that is capable of effecting long term expression of an exogenous gene (e.g., NPY or a functional fragment thereof) in a target cell of the CNS, without causing a clinically unacceptable spectrum of deleterious side effects. Viral and non-viral vectors useful in the methods of the present invention are capable of transducing/transfecting postmitotic cells, such as mature neurons, with high efficiency and stability, while exhibiting minimal immunogenicity and non-pathogenicity.

Other gene delivery systems that provide means for achieving long-term expression of exogenous DNA throughout the brain have been described previously. See U.S. Pat. No. 6,436,708. Such delivery systems may also be applied in the methods of the present invention. Gene delivery methods include, but are not be limited to viral vectors, including adenovirus, AAV, retrovirus, antiviral vectors (including HIV, FIV and EIAV based), HSV, SV40, sindbis, forest semliki and alphaviruses. In addition, non-viral systems including naked DNA, DNA associated with liposomes, polymers and other cationic delivery methods, as well as peptide nucleic acid complexes, nucleic acids associated with protein transduction domains, as well as nucleic acid antibody complexes. For a review of these delivery methods, see Pardridge. (2002) Neuron 36:555-8; Fisher and Ho. (2002) CNS Drugs 16:579-93; Davidson and Breakefield. (2003) Nat Rev Neurosci. 4:353-64.

Adenovirus and Adenovirus Vectors

The adenovirus genome consists of about 36 kb of double-stranded DNA. Adenoviruses target airway epithelial cells, but are capable of infecting neural cells.

Recombinant adenovirus vectors have been used successfully as gene transfer vehicles for non-dividing cells. These vectors are similar to recombinant HSV vectors, since the adenovirus E1a immediate-early gene is removed but most viral genes are retained. Since the E1a gene is small (roughly 1.5 kb) and the adenovirus genome is roughly one-third the size of the HSV genome, other non-essential adenovirus genes are also removed to facilitate insertion of an exogenous gene into an adenovirus genome.

One of the principal advantages of recombinant adenovirus vectors, as compared to HSV vectors, is that diseases resulting from adenovirus infections are not as severe as those induced by HSV infection. Certain complications associated with the use of adenoviral vectors should, however, be taken into consideration when planning a therapeutic regimen wherein these vectors are envisioned. Retention and expression of many adenovirus genes in a recipient cell can lead to cytotoxic effects in the cell. In addition, recombinant adenovirus vectors can elicit immune responses that may serve to both limit the effectiveness of vector-mediated gene transfer and facilitate the destruction of transduced cells. Finally, stability of long-term expression is variable, in part, because there is no mechanism for specific viral integration into the genome of non-dividing host cells at a high frequency.

Upon consideration of the potential pitfalls associated with using these vectors, a skilled practitioner would, however, appreciate that adenoviral vectors may be used advantageously in the method of the present invention. Certain features of these vectors are particularly beneficial for applications directed to gene therapy. Adenovirus particles are stable and can be produced at high titers using procedures that are relatively straightforward. Moreover, the adenoviral genome can be manipulated genetically with ease. Adenovirus vectors are also capable of transducing replicating and nonreplicating cells efficiently in vitro and in vivo.

A number of adenoviral vectors have been described including, first-generation adenoviral vectors wherein the E1A and E1B genes have been deleted [Gilardi et al. (1990) FEBS Letters 267:60-62; Stratford-Perricaudet et al. (1990) Hum. Gene Ther. 1:241-256]. E3 may also be deleted to increase the capacity of the vector to incorporate foreign DNA. The capacity for uptake of foreign DNA is, therefore, about 8 kb. First-generation adenovirus vectors have to date been produced mainly in 293 cells which complement the E1A and E1B deficit of the vectors.

Second-generation adenoviral vectors are characterized by deletions of E2 and/or E4 in addition to deletions of E1A and E1B [Engelhardt et al. (1994) Proc. Natl. Acad. Sci. 91:6196-6200; Yang et al. (1994) Nature Genet. 7:362-367; Gorziglia et al. (1996) J. Virol. 70:4173-4178; Krougliak and Graham (1996) Hum. Gene Ther. 6:1575-1586; Zhou et al. (1996) J. Virol. 70:7030-7038]. E3 may also be deleted to increase the capacity of the vector to incorporate foreign DNA. Second-generation adenoviral vectors express fewer viral genes/proteins, thereby reducing the antigenic triggers that can lead to an antiviral immune response. The capacity for uptake of foreign DNA is negligibly increased by comparison with first-generation adenoviral vectors. Second-generation adenovirus vectors are produced in cell lines which, in addition to E1A and E1B, complement the E2 and/or E4 deficit.

Large capacity adenoviral vectors into which large sequences of exogenous DNA can be incorporated have also been described. Such vectors have essentially been deleted of viral coding DNA sequences [Kochanek et al. (1996) Proc. Natl. Acad. Sci. 93:5731-5736; Fisher et al. (1996) Virology 217:11-22; Kumar-Singh and Chamberlain. (1996) Hum. Mol. Genet. 5:913-921]. These vectors comprise only the viral ends, including the inverted terminal repeats (ITRs) and the packaging signals. The capacity for uptake of foreign DNA is about 37 kb. Various systems have been described for producing adenoviral vectors of large DNA capacity [Kochanek et al., supra; Parks et al. (1996) Proc. Natl. Acad. Sci. 93:13565-13570; Hardy et al. (1997) J. Virol. 71:1842-1849]. Adenoviral vectors with large DNA capacity exhibit improved features as compared to first- and second-generation adenoviral vectors because they have a larger capacity for uptake of foreign DNA, and exhibit reduced toxicity and immunogenicity [Schiedner et al. (1998) Nature Genet. 18:180-183; Morral et al. (1998) Hum. Gene Ther. 9:2709-2716]. Adenoviral vectors of large capacity may be produced with the aid of an EIA- and E1B-deleted helper virus which provides the viral functions necessary for a productive infection cycle in trans. Adenoviral vectors of large DNA capacity can be produced in 293 cells or in cell lines derived from 293 cells. See, for example, Parks et al., supra; and Hardy et al, supra.

Deleted adenoviral vectors have been described which are essentially first-generation vectors which have the loxP recognition sequences of bacteriophage P1 positioned in the viral genome in such a way that, upon infection of Cre-expressing 293 cells, most of the viral coding sequences or all the viral coding sequences are deleted by recombination between the loxP recognition sequences. The size of the genome of these vectors is about 9 kb and the capacity for uptake of foreign DNA is about 9 kb [Lieber et al. (1996) J. Virol. 70, 8944-8960].

For more information on vectors, see also Akli et al. (1993) Nature Genetics 3:224-228; Le Gal La Salle et al. Science 259:988-90 (1993), Le Gal La Salle (1993) Nature Genetics 3:1-2; and Neve (1993) TIBS 16:251-253.

HSV Vectors

HSV vectors may also be used in the method of the present invention. HSV has the ability to infect many tissue types and therefore HSV viral vectors offer a promising system with which to transduce a wide variety of cell types. Latency in HSV infection tends to be established within neuronal cells, though it is possible that expressed gene products may translocate from their original point of production. Recombinant HSV viral vectors, such as those described in U.S. Pat. Nos. 6,613,892 (issued to Preston et al.) and 6,610,287 (issued to Breakefield et al.), are therefore particularly useful for delivering exogenous/heterologous nucleic acid sequences into neuronal cells, wherein they are capable of being expressed. Nucleic acid sequences such as those described herein (i.e., NPY and functional derivatives and fragments thereof) and expression of encoded peptides therefrom confers a therapeutic effect by ameliorating the symptoms associated with a neurological disorder.

Recombinant HSV vectors of the invention may be either HSV-1 or HSV-2 or an intertype recombinant between HSV-1 and HSV-2 that comprises nucleotide sequences derived from both types. The recombinant HSV genome will generally be contained in a mutant HSV virus.

Methods of making recombinant HSV vectors, such as those described in U.S. Pat. No. 6,573,090 (issued to Breakefield et al.), are also encompassed by the present invention.

Lentivirus Vectors

The method of the present invention is also compatible with lentiviral vectors. Examples of lentiviruses from which vectors may be derived include: human immunodeficiency virus (HIV), simian immunodeficiency virus (SIV), feline immunodeficiency virus (FIV), bovine leukemia virus (BLV), equine infectious anemia virus (EIAV), cell-associated enveloped virus (CEV), and visna virus. Lentivirus vector packaging cell lines and methods for producing lentivirus vector stocks have been described previously. See, for example, U.S. Pat. No. 6,613,569 (issued to Dougherty et al.). Additional retroviral vector particles and DNA constructs encoding RNA genomes of retroviral vectors have also been described. See U.S. Pat. No. 6,235,522 (issued to Kingsman et al.). Disarmed lentiviral vectors that direct the synthesis of both lentiviral vector transcripts that can be packaged and lentiviral proteins for rapid production of high titer recombinant lentivirus in mammalian cells have also been described. Cell lines useful for making disarmed lentiviral vectors are also presented. See U.S. Pat. No. 6,428,953 (issued to Naldini et al.)

A skilled artisan would appreciate that a wide variety of expression vectors (viral and non-viral) are available that can be modified to express the DNA sequences of the invention. The specific vectors exemplified herein are merely illustrative, and are not intended to limit the scope of the invention. Alternative expression vectors and methods for their expression are known in the art and described by Sambrook et al. supra or Ausubel et al. supra.

Gene Expression

An exogenous DNA incorporated into an expression vector (e.g., an AAV vector) may comprise a nucleic acid sequence that occurs in nature, a non-naturally occurring nucleic acid sequence which encodes a naturally occurring polypeptide, or a gene which encodes a recognizable mutant of such a polypeptide.

The precise nature of regulatory regions needed for gene expression may vary from organism to organism, but in general include a promoter which directs the initiation of RNA transcription. Such regions may include those 5'-non-coding sequences involved with initiation of transcription such as the TATA box. The promoter may be constitutive or regulatable. Constitutive promoters drive expression of an operably linked gene essentially at all times. Regulatable promoters, on the other hand, can be activated or inactivated in response to regulators, such as cellular conditions or inducer molecules. Regulatable promoters include inducible promoters, which are usually "off", but which may be induced to turn "on", and "repressible" promoters, which are usually "on", but may be turned off. Many different regulators are known to effect control over the activity of regulatable promoters, including temperature, hormones, heavy metals, and regulatory proteins. It is important to note, however, that a constitutive promoter may be somewhat responsive or regulatable under some circumstances.

The regulatability of a promoter may be associated with a particular genetic element, often called an "operator", to which an inducer or repressor binds. The operator may be modified to alter its regulation. Hybrid promoters may be constructed in which the operator of one promoter is transferred into another.

The promoter may be a "ubiquitous" promoter active in essentially all cells of the host organism, e.g., the beta-actin or cytomegalovirus promoters, or it may be a promoter whose expression is more or less specific to a particular type of tissue or target cell. Preferably, a tissue-specific promoter of the invention which is neural specific is essentially only functional in cells of the nervous system. The activity of the promoter optionally may be higher in some cell types or regions of the nervous system than in others.

Thus, the promoter may be active primarily in the central nervous system, or primarily in the peripheral nervous system, or it may be significantly active in both. If it is active in the CNS, it may be specific for the spinal cord, the brainstem (medulla, pons, midbrain, or combinations thereof), the cerebellum, the diencephalon (thalamus and/or hypothalamus), the telencephalon (the corpus striatum and/or the cerebral cortex, and, if the latter, the occipital, temporal, parietal and/or frontal lobes), or combinations thereof. The specificity may be absolute or relative.

Similarly, the promoter may be specific for particular cell types, such as neurons or glial cells in the case of the CNS, or particular receptors or effectors in the case of the PNS. If it is active in glial cells, it may be specific for astrocytes, oligodendrocytes, ependymal cells, Schwann cells, or microglia. If it is active in neurons, it may be specific for particular types of neurons, e.g., motor neurons, sensory neurons, or interneurons. Moreover, the tissue specificity of a promoter may be associated with a particular genetic element, which may be modified, or transferred into a second promoter.

Expression of an exogenous nucleic acid sequence may be achieved using a variety of gene expression control elements. The following provides a list of some of the available means with which to direct expression of operably linked genes. It is by no means comprehensive and should be viewed as providing representative examples of several different categories of regulatory elements.

Expression in All Cell Types

Both strong viral (e.g. immediate early CMV) and relatively non-specific cellular promoters (e.g., beta-actin, Genbank HUMACTBET, K00790) may be used to direct expression in all cell types.

Neuronal Specific Expression

The rat neuron-specific enolase (NSE) promoter (EMBL HSENO2, X51956) is presented as an exemplary promoter for achieving neural specific expression. It will be appreciated that there are a number of other neural specific promoters that may be incorporated into AAV vectors for use in the methods of the present invention. Such neural specific promoters include, but are not limited to, the aromatic amino acid decarboxylase (AADC), neurofilament (GenBank HUM-NFL, L04147), synapsin (GenBank HUMSYNIB, M55301), thy-1 promoter [Chen et al. (1987) Cell 51:7-19], and serotonin receptor (GenBank S62283) promoters, as well as promoters which drive expression of a gene in subpopulations of neural cells such as the tyrosine hydroxylase promoter (TH) (See Nucl. Acids. Res. 15:2363-2384 (1987) and Neuron 6:583-594 (1991)); GnRH promoter (Radovick et al., Proc. Natl. Acad. Sci. USA 88:3402-3406 (1991)); L7 promoter (Oberdick et al., Science 248:223-226 (1990)); DNMT promoter (Bartge et al., Proc. Natl. Acad. Sci. USA 85:3648-3652 (1988)), enkephalin promoter (Comb et al., EMBO J. 17:3793-3805 (1988)); and the MBP promoter; and the like can be utilized. The combination of more broadly active promoters together with silencer elements which restrict expression to neurons is also envisioned.

Glial Specific Expression

Also encompassed by the present invention are expression vectors (e.g., AAV vectors) comprising glial specific promoters or neural/glial specific promoters such as, for example, the glial fibrillary acidic protein (GFAP) promoter (GenBank HUMGFAP, J04569), the S100 promoter (Genbank HUMS100AS, M65210), and the glutamine synthase (EMBL HSGLUS, X59834) promoter.

Neuronal Subpopulation Specific Expression

Other promoters which may be used in the methods of the present invention include peptidergic promoters of: e.g., enkephalin (GenBank HUMENKPH1, K00488), prodynorphin, somatostatin (GenBank RATSOMG, J00787; GenBank HUMSOMI, J00306); monoaminergic promoters of: tyrosine hydroxylase (GenBank M23597), dopamine beta-hydroxylase (GenBank RATDBHDR, M96011), PNMT (EMBL HSPNMTB, X52730); and cholinergic neuron promoters, such as the choline acetyltransferase promoter (GenBank HUMCHAT1, M89915; EMBL HSCHAT, X56585).

For the gene to be expressible, the coding sequence must be operably linked to a promoter sequence functional in the target cell. A promoter region is operably linked to a coding sequence if the promoter is positioned to be capable of effecting transcription of the coding sequence. It is not necessary that two operably linked sequences are contiguous with one another.

If desired, the non-coding region 3' to the gene sequence coding for the desired RNA product may be obtained. This region may be retained for its transcriptional termination regulatory sequences, such as those which provide for termination and polyadenylation. Thus, by retaining the 3'-region naturally contiguous to the coding sequence, the transcriptional termination signals are provided. Alternatively, a 3' region isolated from a different gene may be substituted for that of the endogenous gene.

The woodchuck posttranslational regulatory element (WPRE) and a bovine growth hormone polyA signal are presented as exemplary regulatory elements for expression in transduced neural cells of the invention. It will be appreciated that there are numerous other regulatory elements that can be incorporated into an expression vector (e.g., an AAV vector) for use in the methods of the present invention. Alternatives for the WPRE include, but are not limited to 3' elements associated with improved mRNA trafficking and stability. Elements that may be substituted for the bovine growth hormone polyA signal include, but are not limited to, SV40 early and late polyA as well as synthetic polyA signals. A skilled practitioner would be aware of the features preferred for such regulatory elements and would be aware of which regulatory elements would provide sufficient functionality to be substituted for the regulatory elements exemplified herein.

Target Cells

The target cells of the method of the present invention are cells of the central or peripheral nervous systems of a mammal. In a particular embodiment, the target cells are located in the CNS. In a more particular embodiment, the target cells of the CNS are isolated from or found in the medial temporal lobe (e.g., the hippocampus and/or amygdala), or the temporal cortex of the brain.

In one embodiment, the cells are cultured in vitro. In an alternative embodiment, the cells are part of a living mammal at the time the vector is delivered to the cell. The mammal may be at any stage of development at the time of delivery, e.g., embryonic, fetal, infantile, juvenile, or adult.

The vector may be delivered to cells of the central nervous system, cells of the peripheral nervous system, or both. When the vector is delivered to the cells of the central nervous system, it may be delivered to cells of the spinal cord, brainstem (medulla, pons, and midbrain), cerebellum, diencephalon (thalamus, hypothalamus), telencephalon (corpus striatum, cerebral cortex, or, within the cortex, the occipital, temporal, parietal or frontal lobes), or combinations thereof.

Similarly, within the peripheral nervous system, it may be delivered to cells of the sensory and/or effector pathways.

To deliver the vector specifically to a particular region of the central nervous system, it may be administered by stereotaxic microinjection, as exemplified herein and in U.S. Pat. No. 6,503,888. For example, on the day of surgery, patients have a stereotactic frame base fixed in place (screwed into the skull). The brain with stereotactic frame base (MRI-compatible with fiducial markings) is imaged using high resolution MRI. The MRI images are transferred to a computer equipped with stereotactic software. A series of coronal, sagittal and axial images may be used to determine the target site (site of expression vector injection) and trajectory. The software directly translates the trajectory into three-dimensional coordinates appropriate for the stereotactic frame. Burr holes are drilled above the entry site and the stereotactic apparatus positioned with the needle implanted at the given depth and the expression vector (e.g., an AAV vector) is injected at the identified target sites. In a particular embodiment, the target site is located in the medial temporal lobe (e.g., the hippocampus and/or amygdala), or the cortical region of the brain. Since an AAV vector, for example, integrates into the target cells, rather than producing viral particles, the subsequent spread of the vector is minor, and largely a function of passive diffusion from the site of injection, prior to integration. The degree of diffusion is controlled by adjusting the ratio of vector to fluid carrier.

The dose of an expression vector (e.g., an AAV vector) may be determined by a skilled neurosurgeon, based in part on the number of cells in the area of the brain to be treated and the size of the target site. In a particular embodiment, an AAV vector of the invention, for example, may be administered at a dose of approximately $10^9$ to $10^{13}$ genomic or viral particles.

An expression vector may be delivered intracerebroventricularly, intraparenchymally, and/or intrathecally, depending on the application. Additional routes of administration are directed to local application of an expression vector under direct visualization, e.g., superficial cortical application, or other non-stereotactic application.

For targeting a vector to a particular type of cell, e.g., a neuron, it may be desirable to associate the vector with a homing agent that binds specifically to a surface receptor of the cell. Thus, a vector may be conjugated to a ligand (e.g., enkephalin) for which certain nervous system cells have receptors. The conjugation may be covalent, e.g., a crosslinking agent such as glutaraldehyde, or noncovalent, e.g., the binding of an avidinated ligand to a biotinylated vector. Another form of covalent conjugation is provided by engineering the helper virus used to prepare the vector stock so that one of the encoded coat proteins is a chimera of a native AAV coat protein, for example, and a peptide or protein ligand, such that the ligand is exposed on the surface. Whatever the form of conjugation, such modifications should not substantially interfere either with the integration of the expression vector (e.g., an AAV vector), or with the binding of the ligand to the cellular receptor.

The target cells may be human cells, or cells of other mammals, especially nonhuman primates and mammals of the orders Rodenta (mice, rats, rabbit, hamsters), Carnivora (cats, dogs), and Arteriodactyla (cows, pigs, sheep, goats, horses).

Pharmaceuticals

Pharmaceutical compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents, modulators, or drugs (e.g., antibiotics).

In particular embodiments, the pharmaceutical compositions also contain a pharmaceutically acceptable carrier or excipient. Such materials should be non-toxic and should not interfere with the efficacy of the active ingredient. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences [Mack Pub. Co., 18th Edition, Easton, Pa. (1990)]. The precise nature of the carrier or other material may depend on the route of administration. As described herein, the present invention is directed to administering the expression vectors and compositions thereof of the invention to target cells in the nervous system.

In accordance with the present invention, an expression vector comprising NPY that is to be given to an individual, is administered preferably in a "therapeutically effective amount" or a "prophylactically effective amount" (as the case may be, although prophylaxis may be considered therapy), this being sufficient to show benefit to the individual.

Although the compositions of the invention have been described with respect to human therapeutics, it will be apparent to one skilled in the art that these tools are also useful in animal experimentation directed to developing treatment regimens for animal subjects that have a neurological disorder. Indeed, as described herein, animal subjects which exhibit symptoms characteristic of various neurological disorders have been developed that serve as model systems for human neurological disorders.

The following examples are provided to illustrate certain embodiments of the invention. They are not intended to limit the invention in any way.

Example I

The results presented herein reveal that long-lasting overexpression of NPY following gene transfer mediated by a recombinant adeno-associated viral (AAV) vector dramatically reduces acute kainate seizures and kindling epileptogenesis in a rat model system of human epilepsy. Notably, transgene expression was significantly increased by 7 days and persisted for at least 3 months. Serotype 2 AAV vector increased NPY expression in hilar interneurons, whereas the chimeric serotype 1/2 vector resulted in more widespread expression that also encompassed mossy fibers, pyramidal cells, and the subiculum. EEG seizures induced by intrahippocampal kainate were reduced by 50% to 75% depending on the spread of NPY expression, and seizure onset was markedly delayed. Moreover, in rats injected with chimeric serotype 1/2 vector, status epilepticus was abolished and kindling acquisition was significantly delayed. Thus, targeted NPY gene transfer offers a novel strategy for effective anti-epileptic treatment in drug-resistant human patients.

To address whether augmentation of local inhibitory tone resulting from constitutive overexpression of NPY in the hippocampus would be an effective strategy for inhibition of seizures and epileptogenesis, the present inventors used recombinant adeno-associated viral vectors (rAAV) expressing NPY to treat the condition in an animal model of epilepsy. Of note, rAAV can successfully transduce postmitotic cells, such as mature neurons, with high efficiency and stability, minimal immunogenicity and non-pathogenicity, and broad host and cell range [During. *Adv. Drug Deliv. Rev.* 27, 83-94 (1997)]. Accordingly, a rAAV vector comprising nucleic acid sequences encoding NPY was designed that was capable of constitutively expressing NPY in neurons.

As described herein below, targeted infection of rats with rAAV comprising NPY sequences resulted in an overexpression of NPY in the brain regions infected. Rats in which targeted infection resulted in overexpression of NPY in the hippocampus and surrounding regions exhibited a dramatic reduction in kainic acid-induced EEG seizures, a delay in seizure onset, and impaired kindling epileptogenesis. These data demonstrate the utility of the novel methods of the present invention for the treatment and management of intractable seizures with focal onset, such as, for example, temporal lobe epilepsy.

Methods

Experimental animals. Male Sprague-Dawley adult rats (~220 g, Charles River, Calco, Italy) were used. They were housed at constant temperature (23° C.) and relative humidity (60%) with a fixed 12 h light-dark cycle and free access to food and water. Procedures involving animals and their care were conducted in conformity with institutional guidelines that comply with national and international laws and policies.

Plasmid Construction and AAV Vector Production

The plasmid AAV/NSE-NPY WPRE (AAV-NPY) was constructed using standard molecular cloning procedures. Human pre-pro-NPY (ppNPY) cDNA was subcloned into an expression cassette consisting of the rat neuron-specific enolase (NSE) promoter, woodchuck posttranslational regulatory element (WPRE), and a bovine growth hormone polyA signal. The same expression cassette without the transgene was used as the control (AAV-Empty). Expression cassettes were subcloned into the AAV backbone flanked by AAV2 inverted terminal repeats.

High-titer AAV serotype 2 vectors were generated by packaging the AAV plasmids as described previously [During et al. *Methods Mol. Med.* 76, 221-36 (2003)]. Chimeric AAV 1/2 vectors were packaged using the published protocol with the addition of an AAV 1 capsid helper plasmid in a 1:1 ratio with the AAV2 helper. The presence of AAV2 capsid proteins on the chimeric viral particles enabled their isolation by affinity purification on heparin-agarose columns. Genomic titers of vector stocks were determined using the Perkin-Elmer (PE)-Applied Biosystems (Foster City, Calif.) Prism 7700 sequence detector system as described previously [Clark et al. *J. Drug. Target* 7, 269-83 (1999)].

NPY Gene Delivery

Two different AAV-NSE-NPY vectors were used: either serotype 2 or the chimeric serotype comprising both AAV1 and 2 capsid proteins. rAAV vector was injected bilaterally into both dorsal and ventral aspects of rat hippocampus (3 µl/45 minutes rAAV-NSE-NPY, $4.2 \times 10^8$ each site using a 10 µl Hamilton syringe and infusion pump controlled by a microprocessor) as previously described [Mastakov et al. *Mol. Ther.* 5, 371-80 (2002); Lin et al. *Eur. J. Neurosci.* in press (2003)]. For rats subjected to subsequent intrahippocampal kainic acid injections, rAAV was infused bilaterally into the dorsal hippocampus only. All injections were carried out under stereotactic guidance in Equithesin anaesthetized rats [Vezzani et al. *J. Neurosci.* 19, 5054-65 (1999)]. Controls rats were injected with equivalent volumes of rAAV-NSE-empty.

Kainic Acid

Eight weeks after either rAAV-NSE-NPY or rAAV-empty injection, rats (n=5-10) were implanted under deep Equithesin anaesthesia with hippocampal and cortical electrodes and guide cannulae for drug injection as described by Vezzani et al. [Vezzani et al. *Neuroscience* 110, 237-43 (2002); Vezzani et al. *J. Neurosci.* 19, 5054-65 (1999)]. Four days after surgery, freely-moving rats were unilaterally injected with kainic acid into the dorsal hippocampus (40 ng) or the lateral ventricle (250 ng). EEG recordings were made before (baseline), during and up to 180 minutes after kainic acid administration and analyzed visually to detect any activity that varied from that of baseline as determined by an investigator blinded to the identity of the rats. Seizures consisted of the simultaneous occurrence of high-frequency and/or multi-spike complexes and/or high-voltage synchronized spike or wave activity in cortical and hippocampal leads of recording [Vezzani et al. *Neuroscience* 110, 237-43 (2002); Vezzani et al. *J. Neurosci.* 19, 5054-65 (1999)]. Seizure activity was quantified by measuring the latency to the first seizure (onset), the number of seizures, and their duration in the 3 hours of recording. This experimental model of seizures was chosen since it is known to be highly sensitive to the modulatory effects of NPY receptor ligands [Vezzani et al. *J. Nutr.* 130, 1046S-8S (2000)].

Rapid Kindling

A different group of rats injected 8 weeks before with rAAV-empty vector or chimeric 1/2 AAV-NSE-NPY (n=7-9) was electrically stimulated and EEG recorded in the left ventral hippocampus according to a well established rapid kindling protocol [Kopp et al. *Brain Res. Mol. Brain Res.* 72, 17-29 (1999)] using constant current stimuli (50 Hz, 10 sec trains of 400 µA, 1-msec bipolar square waves) through a bipolar electrode, with a 5-minute interval for 200 minutes. Behavior was observed and scored according to Racine [Racine. *Electroencephalogr. Clin. Neurophysiol.* 32, 281-94 (1972)]. After discharges were measured in the stimulated hippocamus after each stimulation for every animal. Twenty-four hours after kindling completion, fully kindled rats received five additional electrical stimulations (re-test day) as above to confirm kindling maintenance.

In Situ Hybridization Analysis of mRNA

Rats were killed by decapitation eight weeks after rAAV-NSE-NPY or rAAV-empty vector injection (n=3-4), and their brains were rapidly frozen into isopentane (−70° C.). These rats were not subjected to seizures. Coronal sections (20 µm) were cryosectioned, mounted on gelatin-coated slides, and stored at −30° C. In situ hybridization for NPY mRNA was done as described in detail previously [Gruber et al. *Hippocampus* 4, 474-82 (1994)]. A 46-mer oligonucleotide probe (CTCTGTCTGGTGATGAGATTGATGTAGT-GTCGCAGAGCGGAGTAGT; SEQ ID NO: 9) complementary to bases 214-259 (GenBank accession number NM_012614) of ppNPY mRNA was used and radiolabeled with $[^{35}S]$ α-thio-dATP (1300 Ci/mmol; New England Nuclear, Wilmington, Del.) at the 3' end by reaction with terminal deoxynucleotidyl transferase (Roche, Mannheim, Germany). After incubation at 42° C. (18 hrs) and stringent washing, sections were first exposed to BioMax MR films (Amersham Pharmacia Biotech, Buckinghamshire, UK), for 3 days and subsequently dipped in Kodak NTB-2 photosensitive emulsion (Kodak, Rochester, N.Y.; diluted 1:1 with distilled water) and exposed for one week. After developing the photoemulsion and counterstaining with cresyl violet, coverslips were applied to the sections.

Immunohistochemistry

Rats were sacrificed three days to three months after rAAV-NSE-empty or rAAV-NSE-NPY (serotype 2 or 1/2) delivery (n=3 rats each group) by transcardial perfusion with PBS followed by 4% paraformaldehyde in PBS under Equitesin anesthesia [Vezzani et al. *Neuroscience* 110, 237-43 (2002)]. These rats were not subjected to seizures. The brains were post-fixed in the same fixative overnight at 4° C. and then cryoprotected in 30% sucrose in PBS. Forty µm coronal hippocampal sections were cryosectioned in each rat through the entire septo-temporal extension and every fifth section was analyzed. Immunohistochemistry was performed as described [Schwarzer et al. *Brain Res. Brain Res. Rev.* 22, 27-50 (1996)] using a rabbit polyclonal anti-NPY antibody (1:2000 dilution, Chemicon Int, Temecula, Calif.). Immunoreactivity was detected by the avidin-biotin-peroxidase technique (Vectastain ABC kit, Vector Labs, USA) and then developed by incubation with 3',3'-diaminobenzidine (Sigma).

Statistical Analysis

Data are presented as the mean±SEM. One-way ANOVA followed by Tukey's test was used to determine the effects of vector treatment versus AAV-NSE-Empty control.

Results rAAV-NSE-NPY Gene Expression

Local injection of either rAAV-NSE-NPY construct (serotype 2 or serotype 1/2) or empty viral vector caused minimal local neuronal damage, which was restricted to the area adjacent to the needle tract as assessed three days and eight weeks after vector injection by Fluoro Jade or Nissl staining analysis of brain sections [for methodological details see Xu et al. *Gene Ther.* 8, 1323-32 (2001)].

NPY gene overexpression was restricted to the injected hippocampus and extended for ~1.5 mm or ~2.5 mm around the injection site for serotype 2 and serotype 1/2, respectively, as judged by evaluating the area of increased NPY mRNA expression. Corroborative evidence pertaining to the area in which the transduced gene was expressed was obtained by confocal microscope analysis of coronal brain sections from rats injected with rAAV-NSE carrying the green fluorescent protein gene (GFP). NPY gene expression induced by either vector was restricted to neurons, maximal after two weeks, and maintained for at least three months.

Eight weeks after vector injection, serotype 2 rAAV-NSE-NPY induced a marked increase in NPY mRNA hybridization signal in hilar interneurons of the injected dorsal hippocampus, as compared to corresponding sections of rAAV-NSE-empty injected rats. Accordingly, immunocytochemical analysis of coronal brain sections encompassing the injected site (dorsal dentate gyrus) exhibited enhanced NPY immunoreactivity in hilar interneurons, including intensely labeled fibers in the hilus and their terminal projection area in the outer molecular layer. NPY immunoreactivity was increased in the inner molecular layer both in the injected and contralateral hippocampus outlining the region where associational/commissural fibers, arising from mossy cells of the injected dentate hilus, terminate [Laurberg. *J. Comp. Neurol.* 184, 685-708 (1979)].

Under the same experimental conditions described above, serotype 1/2 rAAV-NSE-NPY injected rats displayed high expression of NPY mRNA in hilar interneurons and granule cells, as well as pyramidal cells at the injected site. Strong transcript signal was also observed in the subiculum. Accordingly, immunocytochemical analysis of NPY in the injected hippocampus of chimeric serotype rAAV-NSE-NPY-treated rats showed strongly increased peptide levels in the terminal field of mossy fibers and CA1 pyramidal cells. Hilar interneurons, CA3 pyramidal cells, and the subiculum exhibited enhanced immunoreactivity. Increased NPY immunoreactivity was also found in the inner molecular layer of the contralateral hippocampus and in both inner and outer molecular layers of the injected hippocampus.

Kainic Acid-Induced Seizures

Preliminary experiments demonstrated that 40 ng and 250 ng kainic acid injected unilaterally into the dorsal hippocampus or the lateral ventricle respectively, were the lowest convulsant-promoting doses which resulted in reproducible EEG seizures in 100% of treated rats in the absence of mortality. After either intrahippocampal or intracerebroventricular (icv) injection of kainic acid, all control rats developed discrete episodes of seizures lasting 2.5 minutes on average. See FIG. 2B and [Laurberg. *J. Comp. Neurol.* 184, 685-708 (1979)]. Status epilepticus defined by continuous seizure activity lasting 85 minutes on average, and associated with generalized clonic convulsions, was observed only after icv application of kainic acid (FIG. 2C).

Both rAAV-NSE-NPY vectors significantly reduced seizure activity induced by intrahippocampal application of 40 ng of kainic acid (FIG. 1). Thus, the number of EEG seizures and their duration was decreased by ~50% in serotype 2 rAAV-NSE-NPY injected rats (n=5) and by ~75% in serotype 1/2 rAAV-NSE-NPY injected rats (n=10; p<0.005 compared to AAV2-NSE-NPY); the time to seizure onset was delayed by ~2-fold in both groups (p<0.01 vs rAAV-empty, n=10).

Since serotype 1/2 rAAV-NSE-NPY vector induced a more widespread transduction of the NPY gene resulting in greater seizure reduction, further characterization of seizure susceptibility was performed in rats injected with this vector. Table 1 shows the quantitative evaluation of EEG seizure activity induced in rats by icv administration of 250 ng kainic acid, eight weeks after the intrahippocampal injection of rAAV-NSE-empty (control rats) vs serotype 1/2 rAAV-NSE-NPY. rAAV-NSE-NPY-injected rats had a ~2-fold delay in seizure onset and up to ~76% reduction in total time spent in EEG seizures (p<0.01) due to abolition of status epilepticus (compare FIGS. 2C and 2F).

TABLE 2

Kindling epileptogenesis in rAAV-NSE-NPY injected rats versus rAAV-NSE-empty injected rats.

|  | Empty vector | rAAV-NSE-NPY |
|---|---|---|
| Afterdischarge threshold (µA) | | |
|  | 127 ± 4 | 180 ± 21* |
| Number of electrical stimuli | | |
| Stage 1 | 1.1 ± 0.1 | 1.3 ± 0.1 |
| Stage 2 | 1.4 ± 0.3 | 2.4 ± 0.7 |
| Stage 3 | 6.2 ± 1.8 | 12.8 ± 2.1* |
| Stage 4-5 | 11.4 ± 2.5 | 25.5 ± 4.2** |
| Cumulative afterdischarge (min) | | |
|  | 14.9 ± 2.0 | 9.9 ± 1.0* |

Data are the mean ± SE of kindling parameters (n = 7-9 rats).
Afterdischarge threshold represents the minimum current (µA) inducing afterdischarge in the stimulated hippocampus before the beginning of kindling.
Number of electrical stimuli required for inducing the respective kindling stages are reported.
Cumulative afterdischarge represents the average of the sum of all afterdischarge recorded by EEG following electrical stimulation during kindling.
*$p < 0.05$,
**$p < 0.01$ by Tukeys's test.

TABLE 1

Seizure activity in rats over expressing NPY in the hippocampus 8 weeks after rAAV-NSE- NPY injection.

| Treatment | Onset (min) | Number of seizures | Time in discrete seizures (min) | Time in status epilepticus (min) | Total time in seizures (min) |
|---|---|---|---|---|---|
| rAAV-NSE-Empty | 6.2 ± 0.3 | 18.0 ± 1.0 | 53.5 ± 6.0 | 86.9 ± 10.1 | 137.0 ± 7.9 |
| rAAV-NSE-NPY (serotype ½) | 11.5 ± 1.8** | 23.0 ± 6.0 | 53.4 ± 9.7 | 0 | 53.4 ± 9.7** |

Data are the mean ± SE (n = ~6-15).
Kainic acid was injected intracerebroventricularly (250 ng in 0.5 µl), 8 weeks after vector injection.
**$p < 0.01$ vs rAAV-NSE-Empty by Tukey's test Kindling-Induced Epileptogenesis Development of kindling epileptogenesis was examined and compared in rats injected with either rAAV-NSE-NPY serotype 1/2 vector or rats injected with the empty-vector cassette at eight weeks post-injection. The threshold current for inducing afterdischarge in the stimulated hippocampus before the beginning of kindling was increased by 40% in rAAV-NSE-NPY rats (p<0.05, Table 2). This parameter was not modified in rats injected with serotype 2 rAAV-NSE-NPY vector. The number of stimuli needed to induce preconvulsive stages 1 and 2 was not affected by NPY overexpression, while the number of electrical stimuli needed to induce stage 3 (clonic contraction of back muscles) and stages 4-5 (generalized clonic motor seizures with or without loss of posture) was increased by ~2-fold (p<0.05 and 0.01). The total number of stage 4-5 seizures was lower in rAAV-NSE-NPY injected rats (4±1, n=7, p<0.01) compared to empty vector (9±2, n=9). The average duration of the cumulative afterdischarge occurring during kindling in the stimulated hippocampus was reduced by ~30% (p<0.05).

Discussion

The present inventors have shown for the first time that in vivo ectopic expression of NPY in the hippocampus induced by local application of AAV-based vectors provides significant protection from limbic seizures and impairs epileptogenesis in rats. Gene transduction was observed exclusively in neurons due to a strong neuronal tropism of these vectors [Xu et al. Gene Ther. 8, 1323-32 (2001); Kaplitt et al. Nat. Genet. 8, 148-54 (1994); McCown et al. Brain Res. 713, 99-107 (1996)] and the use of a neuronal specific promoter. Under normal physiological conditions, NPY is constitutively present in interneurons in the hilus, stratum oriens CA1-CA3, and radiatum CA3 [Milner et al. J. Comp. Neurol. 386, 46-59 (1997)]. As described herein, two different patterns of NPY expression were observed in the injected hippocampus depending on the vector serotype used. Utilization of serotype 2 led to robust expression in hilar interneurons, whereas use of chimeric serotype 1/2 resulted in additional expression in pyramidal and granule cells. In the injected hippocampus, NPY was strongly expressed in fibers located in the inner and outer molecular layers of the dentate gyrus and in the terminal field of mossy fibers. Increased NPY immunoreactivity was also specifically observed in the inner molecular layer of the contralateral hippocampus where the commissural fibers terminate. These results demonstrate that NPY is efficiently transported to the nerve terminals after its vector-mediated transduction into cell bodies, and likely exerts therapeutic benefit beyond the focal injection site.

Consistent with the anticonvulsant and antiepileptogenic actions of NPY [Vezzani et al. *Trends Neurosci.* 22, 25-30 (1999); Baraban et al. *J. Neurosci.* 17, 8927-36 (1997); DePrato Primeaux et al. *Neurosci. Lett.* 287, 61-4 (2000); Smialowska et al. *Neuropeptides* 30, 67-71 (1996); Woldbye. *Regul. Pept.* 75-76, 279-82 (1998); Marsh et al. *Proc. Natl. Acad. Sci. USA* 96, 13518-23 (1999); Reibel et al. *Peptides* 22, 529-39 (2001); Husum et al. *Neuropeptides* 36, 363-9 (2002); Mazarati and Wasterlain. *Neurosci. Lett.* 331, 123-7 (2002)], vector-mediated overexpression of this peptide significantly reduced seizure activity induced by intracerebral kainate application. In particular, rats with widespread NPY overexpression (serotype 1/2 vector) displayed greater reduction of discrete seizure episodes, i.e. 75%, compared to 50% decrease observed in rats with NPY overexpression restricted to hilar interneurons. This indicates that NPY expression may efficiently control hippocampal hyperexcitability at multiple synaptic sites, including hilar interneurons, mossy fibers, and terminals of pyramidal and subicular neurons.

Prolonged seizure episodes were typically observed in the hippocampus of rats injected with icv kainate. These episodes were associated with generalized motor seizures, thus likely representing reverberant activity within the limbic circuit. Prolonged seizure episodes were abolished in rats overexpressing NPY in multiple hippocampal subfields indicating that peptide overexpression impairs seizure generalization by enhancing the inhibitory tone within the hippocampus. Similarly, serotype 1/2 virus-mediated NPY overexpression also effectively delayed kindling epileptogenesis, an effect which was apparent from stage 3 to stages 4-5 when generalized motor convulsions occur. These data are in agreement with pharmacological evidence showing that subchronic NPY infusion in the hippocampus retards kindling acquisition [Reibel et al. *Epilepsia* 41 Suppl 6, S127-33 (2000]. The same inhibitory profile on kindling was found in transgenic rats selectively overexpressing NPY in the brain [Vezzani et al. *Neuroscience* 110, 237-43 (2002)].

Despite a pronounced loss of NPY interneurons in the hilar polymoiphic cell layer following severe seizures in experimental models and humans, NPY/GABA containing subgranular interneurons, granule neurons, and in some instances pyramidal cells are generally spared [de Lanerolle et al. *Brain Res.* 495, 387-95 (1989); Mathern et al. *J. Neurosci.* 15, 3990-4004 (1995); Furtinger et al. *J. Neurosci.* 21, 5804-12 (2001); Sloviter. *Hippocampus* 1, 41-66 (1991); Sperk et al. *Neuroscience* 50, 831-46 (1992); Sundstrom et al. *Brain* 124, 688-97 (2001)]. Thus, surviving cells within the sclerotic temporal lobe represent an attractive target population for vector-mediated NPY overexpression. The present inventors have also found that chronic overexpression of NPY in the rat hippocampus does not significantly affect NPY-Y2 receptors [see also Vezzani et al. *Neuroscience* 110, 237-43 (2002); Thorsell et al. *Proc. Natl. Acad. Sci. U S A* 97, 12852-7 (2000)] and there is solid evidence for widespread and pronounced upregulation of hippocampal NPY-Y2 receptors in various animal models of epilepsy and in patients with TLE [Furtinger et al. *J. Neurosci.* 21, 5804-12 (2001); Gobbi et al. *J Neurochem.* 70, 1615-22 (1998); Schwarzer et al. *Mol. Pharmacol.* 53, 6-13 (1998)]. These findings indicate that crucial targets mediating the inhibitory effects of NPY on glutamatergic function, and by extension, on neuronal excitability, are readily available to NPY in epileptic tissue.

An interesting aspect of neuropeptide regulation, which underscores the utility of neuropeptides as target molecules for controlling seizures, pertains to the observation that they are released from neurons at frequencies of stimulation higher than those required for the release of classical neurotransmitters [Hokfelt. *Neuron* 7, 867-79 (1991)]. This implies that NPY exerts its inhibitory actions on neuronal excitability preferentially during epileptic events and to a lesser extent during non-ictal periods [Vezzani et al. *Trends Neurosci.* 22, 25-30 (1999)].

The inhibitory effects mediated by NPY overexpression in the hippocampus following viral vector transduction highlight the utility of such vectors as novel therapeutic reagents for the treatment and management of intractable seizures with focal onset, such as temporal lobe epilepsy. The rapid advancement in recombinant AAV technology has led to production of clinical-grade AAV vectors which can be stereotaxically delivered directly to the seizure focus in patients with intractable TLE. AAV-mediated NPY expression at the seizure focus in these patients would inhibit and/or dampen seizures by increasing the basal inhibitory tone in the hippocampus, thus possibly providing an alternative to surgical resection of the affected brain area or a delay in the necessity of surgery.

Example II

The present inventors have extended and corroborated the results presented in Example I by demonstrating that NPY is released from brain slices taken from animals that were previously injected with AAV-NPY. The data presented in Table 3 and FIG. 7 were generated using brain slices isolated from rats injected with the chimeric vector 1/2 AAV-NPY vector described herein above. As shown in Table 3 and FIG. 7, NPY release from these brain slices is triggered in a potassium-dependent manner, which recapitulates the physiological conditions that stimulate release of endogenous NPY. Release of endogenous NPY from brain slices taken from control animals (previously injected with AAV control vector) is not detectable using the present methods. These results demonstrate that ectopic or exogenous NPY is expressed at higher levels than endogenous NPY when induced in a potassium-dependent manner.

Figure 7:
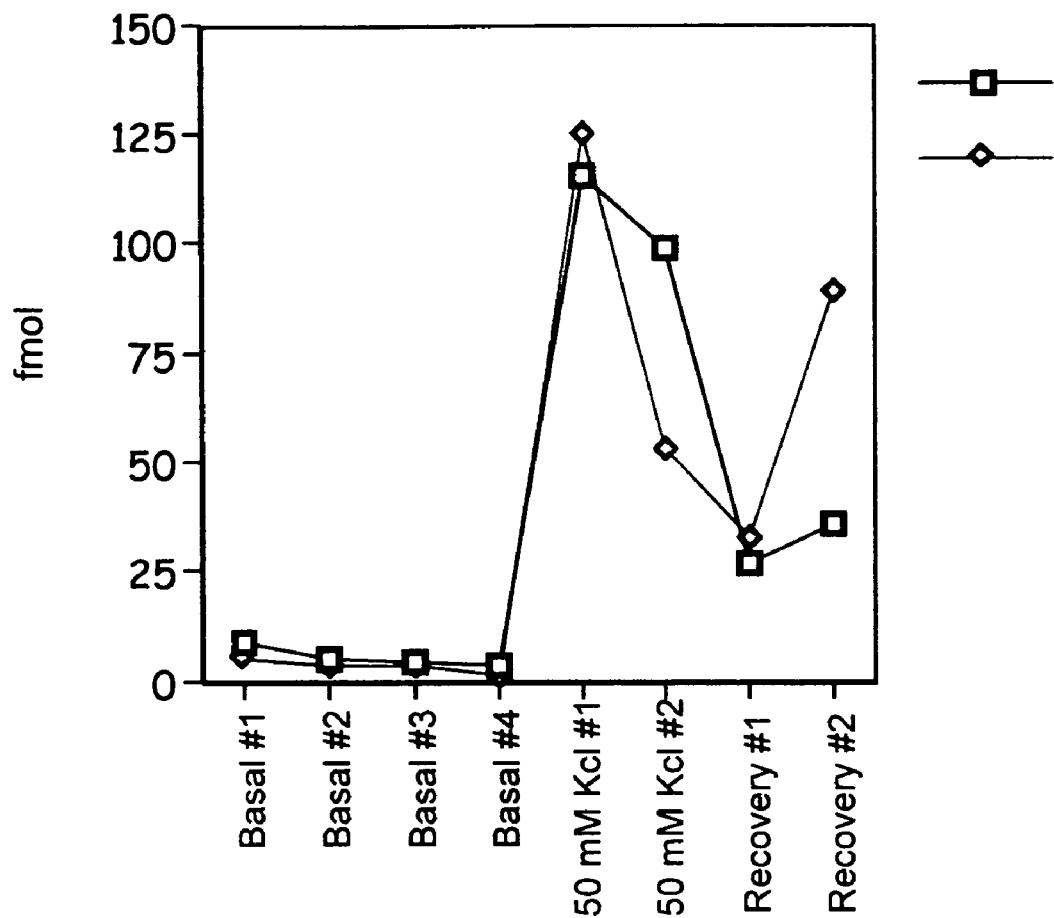
FIG. 7 shows a line graph depicting NPY release from brain slices taken from animals previously injected with AAV-NPY and incubated in vitro as indicated.

The release data shown in Table 3 and FIG. 7 were generated using methodology described previously by Vezzani et al. [Brain Res. 1994, 660(1):138-43] and Rizzi et al. [Eur J. Neurosci. 1993, 5(11):1534-8]. Samples represent 5 minute static incubation of slices in 500 µl medium.

The NPY content in the slices used for release was at least 3-times higher on average in AAV-NPY injected rats vs empty vector-injected rats.

TABLE 3

NPY release from brain slices isolated from rats previously injected with chimeric vector ½ AAV-NPY vector.

|  | AAV-NPY 5 | AAV-NPY 6 |
|---|---|---|
| Basal #1 | 8.3 | 5.16 |
| Basal #2 | 4.8 | 3.54 |
| Basal #3 | 3.8 | 3.54 |
| Basal #4 | 3.7 | 1.4 |
| 50 mM Kcl #1 | 115 | 125 |
| 50 mM Kcl #2 | 99 | 53 |
| Recovery #1 | 26.4 | 33 |
| Recovery #2 | 35.45 | 89 |

Example III

The present inventors have also made the surprising discovery that in animals wherein gene transfer of NPY is achieved using an AAV vector, Y2 subtype NPY receptors are not downregulated, whereas NPY Y1 subtype receptors are down-regulated. See FIGS. 8A-D. This finding is important in the context of the present invention because the Y2 subtype receptors are inhibitory and, in large part, mediate the anti-epileptic and inhibitory effects of NPY. Moreover, the decrease in Y1 subtype NPY receptors is beneficial in the method of the present invention because these receptors mediate excitatory effects of NPY. See Gariboldi et al. [Eur J. Neurosci. 1998, 10(2):757-9 and Benmaamar et al. [Eur J Neurosci. 2003, 18(4):768-74]. In that chronic administration of many growth factors and other proteins is associated with downregulation of their receptors and signal transduction pathways linked to their receptors, the results shown for the NPY Y2 subtype receptor are surprising and lend additional credence to viability of the methods of the present invention.

Methods

AAV Constructs. Chimeric AAV-1/2 vectors/virions comprising minimal promoter and regulatory elements, with or without an NPY transgene, were used to transduce animals from which brain slices were subsequently isolated.

Y1 and Y2 receptor autoradiography. Receptor binding was performed as follows. [Pro$^{34}$]polypeptideYY (PYY) and [$^{125}$I]hPYY3-36 were freshly radioiodinated ([$^{125}$I] was obtained from NEN, Boston, Mass.) using the chloramine T method, and the [$^{125}$I]peptide derivatives were purified by HPLC.

Mounted sections of all sections were processed concomitantly. They were thawed and preincubated in 20 ml Krebs-Henseleit-Tris buffer (118 mM NaCl, 4.8 mM KCl, 1.3 mM MgSO$_4$, 1.2 mM CaCl$_2$, 50 mM glucose, 15 mM NaHCO$_3$, 1.2 mM KH$_2$PO$_4$, 10 mM Tris, pH 7.3) for 60 minutes at room temperature. Incubations were performed in Joplin jars containing 20 ml of the same buffer supplemented with 0.1% bovine serum albumin, 0.05% bacitracin, and the respective radioligand (50 pM [$^{125}$I] [Pro$^{34}$]PYY for Y1-receptor autoradiography or 25 pM [$^{125}$I]PYY3-36 for labeling Y2 receptors) at room temperature for 2 hours. Nonspecific binding was determined in the presence of 1 μM NPY. Sections were dipped twice and then washed in ice-cold Krebs-Henseleit-Tris buffer for 30 seconds, dipped in deionized water, and rapidly dried under a stream of cold air. The slides were then exposed together with [$^{125}$I] microscales to max films (both from Amersham Pharmacia Biotech, Buckinghamshire, UK) for 10 days. For characterization of the receptor binding, NPY, PYY, PYY3-36, PYY13-36, [D-Trp$^{32}$]hNPY, rat pancreatic polypeptide (PP) (all from Neosystem, Strasbourgh, France), [hPP1-17, Ala31, Aib32]NPY and BIBO3304 were used at concentrations of 30-300 nM.

FIGS. 8A-D show representative pictures of Y1 and Y2 subtype receptor binding in AAV-empty and AAV-NPY injected rats (unilateral injections (IPSI) both in dorsal and ventral hippocampi). As shown in FIGS. 8A and 8B (arrowheads) there is a strong decrease in Y1 receptors. In contrast, there is no apparent change in Y2 receptor levels. See FIGS. 8C and 8D. All four rats examined produced similar results. The results shown in FIG. 8 were performed one month after vector injection.

While certain embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating a mammal with temportal lobe epilepsy associated seizures, said method comprising:
   administering a therapeutically effective amount of an adeno-associated virus (AAV) vector to a nervous system target cell in the mammal, wherein said administering is achieved via direct injection into the hippocampus and wherein said AAV vector comprises a nucleic acid sequence encoding exogenous neuropeptide Y;
   expressing said exogenous neuropeptide Y comprising SEQ ID NO: 2, 4, 6, or 8; and
   releasing said exogenous neuropeptide Y from said mammalian nervous system target cell responsive to neuronal stimulation, wherein said exogenous neuropeptide Y release reduces symptoms of the temporal lobe epilepsy, thereby treating the mammal with temporal lobe epilepsy associated seizures.

2. A method for treating a mammal with temporal lobe epilepsy associated seizures, said method comprising:
   administering a therapeutically effective amount of an adeno-associated virus (AAV) vector to a nervous system target cell in the mammal, wherein said administering is achieved via direct injection into the hippocampus and wherein said AAV vector comprises a nucleic acid sequence encoding exogenous neuropeptide Y;
   expressing said exogenous neuropeptide Y comprising SEQ ID NO: 2, 4, 6, or 8; and
   releasing exogenous neuropeptide Y from said mammalian nervous system target cell in a potassium-dependent manner, wherein said exogenous neuropeptide Y release reduces symptoms of the temporal lobe epilepsy, thereby treating the mammal with temporal lobe epilepsy associated seizures.

3. A method for treating a mammal with temporal lobe epilepsy associated seizures, said method comprising:
   administering a therapeutically effective amount of an adeno-associated virus (AAV) vector to a nervous system target cell in the mammal, wherein said administering is achieved via direct injection into the hippocampus and wherein said AAV vector comprises a nucleic acid sequence encoding exogenous neuropeptide Y;
   expressing said exogenous neuropeptide Y comprises SEQ ID NO: 4 or an amino acid sequence at least 97.9% identical to SEQ ID NO: 4; and
   releasing exogenous neuropeptide Y from said mammalian nervous system target cell responsive to neuronal stimulation, wherein said exogenous neuropeptide Y release reduces symptoms of the temporal lobe epilepsy, thereby treating the mammal with temporal lobe epilepsy associated seizures.

4. A method for treating a mammal with temporal lobe epilepsy associated seizures, said method comprising:
   administering a therapeutically effective amount of an adeno-associated virus (AAV) vector to a nervous system target cell in the mammal, wherein said administering is achieved via direct injection into the hippocampus and wherein said AAV vector comprises a nucleic acid sequence encoding exogenous neuropeptide Y;
   overexpressing the exogenous neuropeptide Y, wherein the neuropeptide Y expression is widespread; and reducing seizure activity of the temporal lobe, thereby treating the mammal with temporal lobe epilepsy associated seizures.

5. The method of claim 4, wherein the nucleic acid sequence is selected from the group consisting of SEQ ID NO: 2, SEQ ID NO: 4, SEQ ID NO: 6 or SEQ ID NO: 8.

6. The method of claim 4, wherein the nervous system target cell is at least one of a granule cell, a mossy fiber, a pyramidal neuron and a subicular neuron.

7. The method of claim 4, wherein the AAV vector is a serotype 1/2 vector.

8. The method of claim 4, wherein the step of reducing the seizure activity comprises reducing the number of seizure episodes by between 50% to 75%.

9. The method of claim 4, wherein the step of reducing the seizure activity comprises reducing the number of seizure episodes by about 75%.

10. The method of claim 4, wherein the step of administering is achieved via stereotaxic injection.

11. The method of claim 4, wherein the step of administering further comprises administering the AAV vector in a pharmaceutical composition.

12. The method of claim 11, wherein the pharmaceutical composition further comprises a homing agent.

13. The method of claim 1, wherein the step of administering the therapeutically effective amount of the AAV vector further comprises transducing the target cell with said AAV vector, wherein the AAV vector is free of both wildtype and helper virus.

14. The method of claim 13, wherein the AAV vector is a serotype 2 AAV vector or a chimeric serotype 1/2 AAV vector.

* * * * *

SEQUENCE LISTING

```
<160> NUMBER OF SEQ ID NOS: 9

<210> SEQ ID NO 1
<211> LENGTH: 551
<212> TYPE: DNA
<213> ORGANISM: Homo sapiens

<400> SEQUENCE: 1 acccatccg  ctggctctca  ccctcggag   acgctcgccc  gacagcatag  tacttgccgc    60
ccagccacgc  ccgcgcgcca  gccaccatgc  taggtaacaa  gcgactgggg  ctgtccggac   120
tgaccctcgc  cctgtccctg  ctcgtgtgcc  tgggtgcgct  ggccgaggcg  taccctcca   180 agccggacaa  cccgggcgag  gacgcaccag  cggaggacat  ggccagatac  tactcggcgc   240
tgcgacacta  catcaacctc  atcaccaggc  agagatatgg  aaaacgatcc  agcccagaga   300
cactgatttc  agacctcttg  atgagagaaa  gcacagaaaa  tgttcccaga  actcggcttg   360
aagaccctgc  aatgtggtga  tgggaaatga  gacttgctct  ctggcctttt  cctattttca   420
gcccatattt  catcgtgtaa  aacgagaatc  cacccatcct  accaatgcat  gcagccactg   480
tgctgaattc  tgcaatgttt  tcctttgtca  tcattgtata  tatgtgtgtt  taaataaagt    540
atcatgcatt  c                                                           551

<210> SEQ ID NO 2
<211> LENGTH: 97
```

<212> TYPE: PRT
<213> ORGANISM: Homo sapiens

<400> SEQUENCE: 2

```
Met Leu Gly Asn Lys Arg Leu Gly Leu Ser Gly Leu Thr Leu Ala Leu
  1               5                  10                  15
Ser Leu Leu Val Cys Leu Gly Ala Leu Ala Glu Ala Tyr Pro Ser Lys
             20                  25                  30
Pro Asp Asn Pro Gly Glu Asp Ala Pro Ala Glu Asp Met Ala Arg Tyr
             35                  40              45
Tyr Ser Ala Leu Arg His Tyr Ile Asn Leu Ile Thr Arg Gln Arg Tyr
 50                  55                  60
Gly Lys Arg Ser Ser Pro Glu Thr Leu Ile Ser Asp Leu Leu Met Arg
 65                  70                  75                  80
Glu Ser Thr Glu Asn Val Pro Arg Thr Arg Leu Glu Asp Pro Ala Met
                 85                  90                  95
Trp
```

<210> SEQ ID NO 3
<211> LENGTH: 411
<212> TYPE: DNA
<213> ORGANISM: Macaca mulatta

<400> SEQUENCE: 3

```
gccagccacc atgctaggta gcaagcgact ggggctgtcc ggactgaccc tcgccctgtc     60
cctgctcgtg tgcctgggtg cgctggccga ggcgtaccct tccaaaccgg acaacccggg   120
cgaggacgcg ccagcggagg acatggccag atactactcg gcgctgcgac actacatcaa   180
cctcatcacc aggcagaggt atggcaaacg atctagccca gagacactga tttcagacct   240
cttgatgaga gaaagcacag aaaatgttcc cagaactcgg cttgagaccc ttcaatgtgg   300
gtgatgggaa atgaaacttg ctctctgatc ttttcctatt ttcagcccat atttcatcgt   360
gtaaaatgag agtccaccca tcctaccaat gcatgcagcc actgtgctga a             411
```

<210> SEQ ID NO 4
<211> LENGTH: 97
<212> TYPE: PRT
<213> ORGANISM: Macaca mulatta

<400> SEQUENCE: 4

```
Met Leu Gly Ser Lys Arg Leu Gly Leu Ser Gly Leu Thr Leu Ala Leu
  1               5                  10                  15
Ser Leu Leu Val Cys Leu Gly Ala Leu Ala Glu Ala Tyr Pro Ser Lys
             20                  25                  30
Pro Asp Asn Pro Gly Glu Asp Ala Pro Ala Glu Asp Met Ala Arg Tyr
             35                  40                  45
Tyr Ser Ala Leu Arg His Tyr Ile Asn Leu Ile Thr Arg Gln Arg Tyr
 50                  55                  60
Gly Lys Arg Ser Ser Pro Glu Thr Leu Ile Ser Asp Leu Leu Met Arg
 65                  70                  75                  80
Glu Ser Thr Glu Asn Val Pro Arg Thr Arg Leu Glu Asp Pro Ser Met
                 85                  90                  95
Trp
```

<210> SEQ ID NO 5
<211> LENGTH: 561
<212> TYPE: DNA

<213> ORGANISM: Mus musculus

<400> SEQUENCE: 5

| | |
|---|---:|
| gtggatctct tctctcacag aggcacccag agcagagcac ccgccgctca gcgacgactg | 60 |
| cccgcccgcc acgatgctag gtaacaagcg aatggggctg tgtggactga ccctcgctct | 120 |
| atctctgctc gtgtgtttgg cattctggct gaggggtac ccctccaagc cggacaatcc | 180 |
| gggcgaggac gcgccagcag aggacatggc cagatactac tccgctctgc gacactacat | 240 |
| caatctcatc accagacaga gatatggcaa gagatccagc cctgagacac tgatttcaga | 300 |
| cctcttaatg aaggaaagca cagaaaacgc cccagaaca aggcttgaag acccttccat | 360 |
| gtggtgatgg gaaatgaaac ttgttctccc gacttttcca gtttccacc ctcatctcat | 420 |
| ctcatcccct gaaccagtc tgcctgtccc accaatgcat gccaccacta ggctggactc | 480 |
| cgccccattt cccttgttgt tgttgttgta tatatgtgtg tttaaataaa gtaccatgca | 540 |
| ttcaaaaaaa aaaaaaaaa a | 561 |

<210> SEQ ID NO 6
<211> LENGTH: 97
<212> TYPE: PRT
<213> ORGANISM: Mus musculus

<400> SEQUENCE: 6

```
Met Leu Gly Asn Lys Arg Met Gly Leu Cys Gly Leu Thr Leu Ala Leu
 1               5                  10                  15

Ser Leu Leu Val Cys Leu Gly Ile Leu Ala Glu Gly Tyr Pro Ser Lys
            20                  25                  30

Pro Asp Asn Pro Gly Glu Asp Ala Pro Ala Glu Asp Met Ala Arg Tyr
        35                  40                  45

Tyr Ser Ala Leu Arg His Tyr Ile Asn Leu Ile Thr Arg Gln Arg Tyr
    50                  55                  60

Gly Lys Arg Ser Ser Pro Glu Thr Leu Ile Ser Asp Leu Leu Met Lys
65                  70                  75                  80

Glu Ser Thr Glu Asn Ala Pro Arg Thr Arg Leu Glu Asp Pro Ser Met
                85                  90                  95

Trp
```

<210> SEQ ID NO 7
<211> LENGTH: 539
<212> TYPE: DNA
<213> ORGANISM: Rattus norvegicus

<400> SEQUENCE: 7

| | |
|---|---:|
| caagctcatt cctcgcagag gcgcccagag cagagcaccc gctgcgcaga gaccacagcc | 60 |
| cgcccgccat gatgctaggt aacaaacgaa tggggctgtg tggactgacc ctcgctctat | 120 |
| ccctgctcgt gtgtttgggc attctggctg aggggtaccc ctccaagccg acaatccgg | 180 |
| gcgaggacgc gccagcagag gacatggcca gatactactc cgctctgcga cactacatca | 240 |
| atctcatcac cagacagaga tatgcaaga gatccagccc tgagacactg atttcagatc | 300 |
| tcttaatgag agaaagcaca gaaaatgccc ccagaacaag gcttgaagac cttccatgt | 360 |
| ggtgatggga aatgaaactt gctctcctga cttttcctag tttccccccca catctcatct | 420 |
| catcctgtga aaccagtctg cctgtcccac ccaatgcatg ccaccaccag gctggattcc | 480 |
| gacccatttc ccttgttgtc gttgtatata tgtgtgttta aataaagtat catgcattc | 539 |

```
<210> SEQ ID NO 8
<211> LENGTH: 98
<212> TYPE: PRT
<213> ORGANISM: Rattus norvegicus

<400> SEQUENCE: 8

Met Met Leu Gly Asn Lys Arg Met Gly Leu Cys Gly Leu Thr Leu Ala
1               5                   10                  15

Leu Ser Leu Leu Val Cys Leu Gly Ile Leu Ala Glu Gly Tyr Pro Ser
            20                  25                  30

Lys Pro Asp Asn Pro Gly Glu Asp Ala Pro Ala Glu Asp Met Ala Arg
            35                  40                  45

Tyr Tyr Ser Ala Leu Arg His Tyr Ile Asn Leu Ile Thr Arg Gln Arg
    50                  55                  60

Tyr Gly Lys Arg Ser Ser Pro Glu Thr Leu Ile Ser Asp Leu Leu Met
65                  70                  75                  80

Arg Glu Ser Thr Glu Asn Ala Pro Arg Thr Arg Leu Glu Asp Pro Ser
                85                  90                  95

Met Trp

<210> SEQ ID NO 9
<211> LENGTH: 46
<212> TYPE: DNA
<213> ORGANISM: Artificial Sequence
<220> FEATURE:
<223> OTHER INFORMATION: synthetic 46-mer oligonucleotide probe
      complementary to bases 214-259 of SEQ ID NO: 7

<400> SEQUENCE: 9
ctctgtctgg tgatgagatt gatgtagtgt cgcagagcgg agtagt                46
```